(12) United States Patent
Hicks et al.

(10) Patent No.: US 10,245,185 B2
(45) Date of Patent: Apr. 2, 2019

(54) WOUND CONTACTING MEMBERS AND METHODS

(75) Inventors: John Kenneth Hicks, Pocklington (GB); Elizabeth Mary Huddleston, Copmanthorpe (GB)

(73) Assignee: Smith & Nephew PLC, London (GB)

( * ) Notice: Subject to any disclaimer, the term of this patent is extended or adjusted under 35 U.S.C. 154(b) by 1234 days.

(21) Appl. No.: 14/124,613

(22) PCT Filed: Jun. 7, 2012

(86) PCT No.: PCT/GB2012/000489
§ 371 (c)(1),
(2), (4) Date: Jun. 17, 2014

(87) PCT Pub. No.: WO2012/168678
PCT Pub. Date: Dec. 13, 2012

(65) Prior Publication Data
US 2014/0296804 A1    Oct. 2, 2014

(30) Foreign Application Priority Data

Jun. 7, 2011 (GB) .................................. 1109497.6
Jun. 7, 2011 (GB) .................................. 1109500.7
Jun. 7, 2011 (GB) .................................. 1109502.3

(51) Int. Cl.
*A61M 1/00* (2006.01)
*A61F 13/00* (2006.01)

(52) U.S. Cl.
CPC ..... *A61F 13/00068* (2013.01); *A61M 1/0088* (2013.01); *A61F 2013/0028* (2013.01); *A61F 2013/00174* (2013.01)

(58) Field of Classification Search
CPC ...... A61F 13/00068; A61F 2013/00174; A61F 2013/0028; A61M 1/0088
USPC ........................................................ 604/317
See application file for complete search history.

(56) References Cited

U.S. PATENT DOCUMENTS

| | | | |
|---|---|---|---|
| 3,367,332 A | 2/1968 | Groves | |
| 3,486,504 A | 12/1969 | Austin, Jr. | |
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |

(Continued)

FOREIGN PATENT DOCUMENTS

| | | |
|---|---|---|
| CN | 101360521 A | 2/2009 |
| CN | 103501709 A | 1/2014 |

(Continued)

OTHER PUBLICATIONS

US 6,216,701 B1, 04/2001, Heaton et al. (withdrawn)

(Continued)

*Primary Examiner* — Andrew J Mensh
(74) *Attorney, Agent, or Firm* — Knobbe, Martens, Olson & Bear, LLP

(57) ABSTRACT

Wound contacting members and methods, apparatuses, systems and kits incorporating the same are disclosed. The wound contacting members offer improved performance in terms of preventing or inhibiting tissue in-growth and improving tissue granulation growth. The wound contacting members may be used in negative pressure wound therapy (NPWT) applications.

17 Claims, 14 Drawing Sheets

15 ppi 30 ppi 45 ppi 60 ppi

(56) References Cited

U.S. PATENT DOCUMENTS

| | | |
|---|---|---|
| 3,929,135 A | 12/1975 | Thompson |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,266,545 A | 5/1981 | Moss |
| 4,382,441 A | 5/1983 | Svedman |
| 4,508,256 A | 4/1985 | Radek et al. |
| 4,524,064 A | 6/1985 | Nambu |
| 4,710,165 A | 12/1987 | McNeil et al. |
| 4,743,232 A | 5/1988 | Kruger |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,261,893 A | 11/1993 | Zamierowski |
| 5,263,922 A | 11/1993 | Soya et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,562,107 A | 10/1996 | Lavendar et al. |
| 5,588,958 A | 12/1996 | Cunningham et al. |
| 5,636,643 A | 6/1997 | Argenta et al. |
| 5,645,081 A | 7/1997 | Argenta et al. |
| 5,678,564 A * | 10/1997 | Lawrence ............... A61F 5/455 600/573 |
| 5,701,917 A | 12/1997 | Khouri |
| 5,733,305 A | 3/1998 | Fleischmann |
| 5,779,657 A | 7/1998 | Daneshvar |
| 5,840,049 A | 11/1998 | Tumey et al. |
| 5,851,461 A | 12/1998 | Bakis et al. |
| 5,851,648 A | 12/1998 | Stone et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Tumey |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,261,679 B1 | 7/2001 | Chen et al. |
| 6,325,788 B1 | 12/2001 | McKay |
| 6,345,623 B1 | 2/2002 | Heaton et al. |
| 6,348,423 B1 | 2/2002 | Griffiths et al. |
| 6,398,767 B1 | 6/2002 | Fleischmann |
| 6,406,447 B1 | 6/2002 | Thrash et al. |
| 6,406,648 B1 | 6/2002 | Noel et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,689,986 B2 | 2/2004 | Patel et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,776,769 B2 | 8/2004 | Smith |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 * | 6/2008 | Hunt ............... A61M 1/0088 602/42 |
| 7,381,860 B2 | 6/2008 | Gundnason et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,494,482 B2 | 2/2009 | Orgill et al. |
| 7,534,927 B2 | 5/2009 | Lockwood |
| 7,569,742 B2 | 8/2009 | Haggstrom et al. |
| 7,612,247 B2 | 11/2009 | Oyaski |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,722,582 B2 | 5/2010 | Lina et al. |
| 7,723,560 B2 | 5/2010 | Lockwood et al. |
| 7,731,702 B2 | 6/2010 | Bybordi et al. |
| 7,758,554 B2 | 7/2010 | Lina et al. |
| 7,776,028 B2 | 8/2010 | Miller et al. |
| 7,846,141 B2 | 12/2010 | Weston |
| 7,884,258 B2 | 2/2011 | Boehringer et al. |
| 7,896,856 B2 | 3/2011 | Petrosenko et al. |
| 7,909,805 B2 | 3/2011 | Weston |
| 7,910,791 B2 | 3/2011 | Coffey |
| 7,927,318 B2 | 4/2011 | Risk, Jr. et al. |

(56) References Cited

U.S. PATENT DOCUMENTS

| | | |
|---|---|---|
| 7,927,319 B2 | 4/2011 | Lawhorn |
| 7,976,519 B2 | 7/2011 | Bubb et al. |
| 8,034,037 B2 | 10/2011 | Adams et al. |
| 8,062,272 B2 | 11/2011 | Weston |
| 8,067,662 B2 | 11/2011 | Aali et al. |
| 8,096,979 B2 | 1/2012 | Lina et al. |
| 8,168,848 B2 | 5/2012 | Lockwood et al. |
| 8,192,409 B2 | 6/2012 | Hardman et al. |
| 8,535,296 B2 | 9/2013 | Blott et al. |
| 8,613,734 B2 | 12/2013 | Lina et al. |
| 8,708,984 B2 | 4/2014 | Robinson et al. |
| 8,791,316 B2 | 7/2014 | Greener |
| 8,815,594 B2 | 8/2014 | Harris et al. |
| 9,044,579 B2 | 6/2015 | Blott et al. |
| 9,180,231 B2 | 11/2015 | Greener |
| 9,220,822 B2 | 12/2015 | Hartwell et al. |
| 9,271,837 B2 | 3/2016 | Swain |
| 9,895,270 B2 | 2/2018 | Coward et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2002/0161346 A1 | 10/2002 | Lockwood et al. |
| 2003/0078532 A1 | 4/2003 | Ruszczak et al. |
| 2003/0093041 A1 | 5/2003 | Risk, Jr. et al. |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0093026 A1 | 5/2004 | Weidenhagen et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0249353 A1 | 12/2004 | Risk, Jr. et al. |
| 2004/0260230 A1 | 12/2004 | Randolph |
| 2005/0020955 A1 | 1/2005 | Sanders et al. |
| 2005/0085795 A1 | 4/2005 | Lockwood |
| 2005/0090787 A1 | 4/2005 | Risk et al. |
| 2005/0124709 A1* | 6/2005 | Krueger .............. A61L 15/225 521/50 |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2006/0029650 A1 | 2/2006 | Coffey |
| 2006/0039742 A1 | 2/2006 | Cable et al. |
| 2006/0100586 A1 | 5/2006 | Karpowicz |
| 2006/0149170 A1 | 7/2006 | Boynton et al. |
| 2007/0005028 A1 | 1/2007 | Risk et al. |
| 2007/0014837 A1 | 1/2007 | Johnson et al. |
| 2007/0016152 A1 | 1/2007 | Karpowicz et al. |
| 2007/0021697 A1* | 1/2007 | Ginther ................. A61K 33/38 602/1 |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0066925 A1 | 3/2007 | Gudnason et al. |
| 2007/0178145 A1 | 8/2007 | Chou et al. |
| 2007/0179460 A1 | 8/2007 | Adahan |
| 2007/0219513 A1 | 9/2007 | Lina et al. |
| 2007/0225663 A1 | 9/2007 | Watt et al. |
| 2007/0293830 A1 | 12/2007 | Martin |
| 2007/0299369 A1 | 12/2007 | Babaev |
| 2008/0071235 A1 | 3/2008 | Locke et al. |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2008/0300555 A1 | 12/2008 | Olson et al. |
| 2008/0317826 A1 | 12/2008 | Kelly et al. |
| 2009/0105671 A1* | 4/2009 | Daggar ................ D01D 5/0084 604/305 |
| 2009/0204423 A1 | 8/2009 | DeGheest et al. |
| 2009/0299341 A1 | 12/2009 | Kazala et al. |
| 2010/0022972 A1 | 1/2010 | Lina et al. |
| 2010/0063484 A1 | 3/2010 | Heagle |
| 2010/0160874 A1* | 6/2010 | Robinson ............ A61M 1/0023 604/313 |
| 2010/0160876 A1 | 6/2010 | Robinson et al. |
| 2010/0262092 A1 | 10/2010 | Hartwell |
| 2010/0269491 A1 | 10/2010 | Boorse et al. |
| 2010/0305526 A1 | 12/2010 | Robinson et al. |
| 2011/0270202 A1 | 11/2011 | Boehringer et al. |
| 2011/0282309 A1 | 11/2011 | Adie et al. |
| 2012/0083755 A1 | 4/2012 | Lina et al. |
| 2013/0211349 A1 | 8/2013 | Stokes et al. |
| 2015/0159066 A1 | 6/2015 | Hartwell et al. |
| 2016/0256673 A1 | 9/2016 | Heagle |

FOREIGN PATENT DOCUMENTS

| | | |
|---|---|---|
| DE | 4 111 122 A1 | 4/1993 |
| DE | 295 04 378 U1 | 10/1995 |
| EP | 0 020 662 B1 | 7/1984 |
| EP | 0 358 302 A2 | 3/1990 |
| EP | 0 853 950 A1 | 7/1998 |
| EP | 1 169 071 A1 | 4/2000 |
| EP | 1 088 569 A2 | 4/2001 |
| EP | 1 219 311 A2 | 7/2002 |
| EP | 2 255 837 A1 | 12/2010 |
| EP | 2 366 721 A1 | 9/2011 |
| EP | 1 169 071 B1 | 2/2012 |
| EP | 2 160 166 B1 | 1/2014 |
| GB | 1549756 A | 8/1979 |
| GB | 2195255 A | 4/1988 |
| GB | 2235877 A | 3/1991 |
| GB | 2307180 A | 5/1997 |
| GB | 2329127 A | 3/1999 |
| GB | 2336546 A | 10/1999 |
| GB | 2344531 B | 7/2000 |
| GB | 2365350 B | 8/2004 |
| GB | 2415908 | 1/2006 |
| GB | 2415908 A | 1/2006 |
| JP | S47-039481 | 11/1972 |
| JP | S46-103782 | 12/1973 |
| JP | 2011-516199 | 5/2011 |
| JP | 2012-513825 | 6/2012 |
| JP | 2012-528680 | 11/2012 |
| RU | 62504 | 4/2007 |
| SU | 1818103 | 5/1993 |
| SU | 1762940 | 1/2001 |
| WO | WO 1980/01139 | 6/1980 |
| WO | WO 1980/02182 | 10/1980 |
| WO | WO 1984/01904 | 5/1984 |
| WO | WO 1989/05133 | 6/1989 |
| WO | WO 1990/11795 | 10/1990 |
| WO | WO 1992/19313 | 11/1992 |
| WO | WO 1993/09727 | 5/1993 |
| WO | WO 1994/20041 | 9/1994 |
| WO | WO 1996/05873 | 2/1996 |
| WO | WO 2000/21586 | 4/2000 |
| WO | WO 01/85248 | 11/2001 |
| WO | WO 02/092783 | 11/2002 |
| WO | WO 2003/005943 | 1/2003 |
| WO | WO 2003/018098 | 3/2003 |
| WO | WO 2003/030966 | 4/2003 |
| WO | WO 2003/045492 | 6/2003 |
| WO | WO 2003/057070 | 7/2003 |
| WO | WO 2003/057307 | 7/2003 |
| WO | WO 2003/086232 | 10/2003 |
| WO | WO 2003/092620 | 11/2003 |
| WO | WO 2003/101508 | 12/2003 |
| WO | WO 2004/018020 | 3/2004 |
| WO | WO 2005/009488 | 2/2005 |
| WO | WO 2005/105174 | 11/2005 |
| WO | WO 2006/046060 | 5/2006 |
| WO | WO 2006/105892 | 10/2006 |

(56) References Cited

FOREIGN PATENT DOCUMENTS

| | | |
|---|---|---|
| WO | WO 2008/091521 | 7/2008 |
| WO | WO 2008/141228 | 11/2008 |
| WO | WO 2009/021523 | 2/2009 |
| WO | WO 2009/089016 | 7/2009 |
| WO | WO 2009/126102 | 10/2009 |
| WO | WO 2010/141271 | 12/2010 |
| WO | WO 2011/135284 | 11/2011 |
| WO | WO 2012/097381 | 7/2012 |
| WO | WO 2012/168678 | 12/2012 |
| WO | WO 2013/136181 | 11/2013 |
| WO | WO 2015/123609 | 8/2015 |
| WO | WO 2015/148636 | 10/2015 |
| WO | WO 2015/175270 | 11/2015 |

OTHER PUBLICATIONS

US 7,186,244 B1, 03/2007, Hunt et al. (withdrawn)
International Search Report for International Application No. PCT/GB2012/000489 dated Aug. 23, 2012 in 5 pages.
Heit et al., "Foam Pore Size is a Critical Interface Parameter of Suction-Based Wound Healing Devices" Plastic and Reconstructive Surgery, Mar. 2012, p. 589-597.
Heit et al., Waveform and foam pore size optimization of the Vacuum Assisted Closure Device, Freitag, Apr. 16, 2010, p. 12-16.
Search Report of the Intellectual Property Office of the United Kingdom dated Oct. 7, 2011 for Application No. GB1109502.3 in 1 page.
Search Report of the Intellectual Property Office of the United Kingdom dated Oct. 7, 2011 for Application No. GB1109500.7 in 2 pages.
Search Report of the Intellectual Property Office of the United Kingdom dated Sep. 30, 2011 for Application No. GB1109497.6 in 1 page.
Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Chariker, M.E., et al, "Effective Management of Incisional and Cutaneous Fistulae with Closed Suction Wound Drainage," Contemporary Surgery. Jun. 1989, pp. 59-63, vol. 34.
Davydov, Y.A., et al., The Bacteriological & Cytological Assessment of Vacuum Therapy of Purulent Wounds, Vestnik Chirurgia 1988, Oct. Edition 48-52 (in Russian with English translation). 1987.
Fleischmann et al., "Vacuum Sealing: Indication, Technique, and Results", Eur J Orthop Surg Traumatol, (1995) 5:37-40.
Gorica Zivadinovic, et al., "Vacuum Therapy in the Treatment of Peripheral Blood Vessels", Conference Papers of the 5th Timok Medical Days, Majdanpek, 1986 pp. 161-164.
Jeter, K. et al., "Managing Draining Wounds and Fistulae: New and Established Methods", Chronic Wound Care pp. 240-246, 1990.
Kostiuchenok, et al., "The Vacuum Effect in the Surgical Treatment of Purulent Wounds," Russian Journal: Vestnik Khirurgii, Sep. 1986, (18-21).
Mexican Office Action, re MX App. No. MX/a/2013/014422, dated May 11, 2016.
Meyer, W. et al., "In Surgery, Medicine, and the Specialties A Manual of its Practical Application", Bier's Hyperemic Treatment, Second Revised Edition, W B. Saunders Company 1909.
Mulder, G.D., Ed., et al., "Clinicians' Pocket Guide to Chronic Wound Repair", Wound Healing Publications, Spartanburg, SC, 1991, 54-55.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (323-326).
Sandén, Göran Md., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Svedman, et al., "Staphylococcal Wound Infection in the Pig: Part I. Course," Annals of Plastic Surgery, vol. 23, No. 3, Sep. 1989 (212-218).
Usupov, et al., "Active Wound Drainage," Russian Journal: Vestnik Khirugii, Apr. 1987, (42-45).
Yu A. Davydov, et al., "Vacuum Therapy in treatment of Acute Purulent Diseases of Soft Tissues and Purulent Wounds", Vestnik Khirurgii, (Surgeon's Herald), Medicine Publishers, 1986.
Aubrey, D.A. et al., Treatment of the Perineal Wound after Proctectomy by Intermittent Irrigation, Arch. Surg., Oct. 1984, 119, 1141-1144.
Bier, A., Hyperemia as a Therapeutic Agent, Ed. Dr. Gustavus M. Blech, A. Robertson & Co., Chicago 1905.
Bucalo et al. "Inhibition of Cell Proliferation by Chronic Wound Fluid." Wound Repair and Regeneration. Miami, 1993. pp. 181-186.
Chan, N. et al., "Microscopic examination of the microstructure and deformation of conventional and auxetic foams," Journal of Materials Science, vol. 32, Oct. 1997, pp. 5725-5736.
Chardak et al., "Experimental Studies on Synthetic Substitutes for Skin and Their Use in the Treatment of Burns," Annals of Surgery, 1961, vol. 155, No. 1, pp. 127-139.
Davydov, et al., "Concepts for Clinical Biological Management of the Wound Process in the Treatment of Purulent Wounds Using Vacuum Therapy," Vestnik Khirugii, Feb. 1991, 132-135).
Davydov, et al., "Vacuum Therapy in the Treatment of Purulent Lactation Mastitis," Russian Journal: Vesnik Khirurgii, Sep. 1986, (66-70).
Edlich et al., "Evaluation of a New, improved Surgical Drainage System," The American Journal of Surgery, Feb. 1985, pp. 295-298, vol. 149, Issue 2.
Fleischmann, W. Wund Forum Spezia!, "Vakuumversiegelung zur Behandlung von Problemwunden" (with English translation: Vacuum Sealing for Treatment of Problematical Wounds), IHW '94, 6 pages.
Garcia-Rinaldi, R., et al., Improving the Efficiency of Wound Drainage Catheters, Amer. Journ. of Surg., Sep. 1975, 130, 372-373.
Health Technology, Literature R., "Vacuum Assisted Closure Therapy for Wound Care", Health Technology Literature Review (Dec. 2004), 3-59.
International Search Report, re PCT Application No. PCT/US09/48351, dated Nov. 13, 2009.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
McLaughlan, James, Sterile Microenvironment for Postoperative Wound Care, The Lancet, pp. 503-504, Sep. 2, 1978.
Morykwas, M. J., et al., "Vacuum-Assisted Closure: A New Method for Wound Control and Treatment: Animal Studies and Basic Foundation," Annals of Plastic Surgery 38 (1997) 553-562.
RENASYS EZ System for Negative Pressure Wound Therapy, Smith & Nephew announcement, dated Feb. 24, 2009, in 4 pages.
Sames, C.P., Sealing of Wounds with Vacuum Drainage, Br. Med. Journ., Nov. 5, 1977, p. 1223, Correspondence.
Stewart, Joanne, Ph.D., World Wide Wounds—Next generation of products for wound management—2002 (13 pages).
Stoll, "Energetic Remedies—Cupping: Healing Within a Vacuum," https:l/www.suite101.com/article.cfm/ energetic)remedies/74531, Apr. 13, 2005.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Teder and Svedman et al., "Continuous Wound Irrigation in the Pig," Journal of Investigative Surgery, 1990, vol. 3, pp. 399-407.

(56) References Cited

OTHER PUBLICATIONS

Tribble, David E. M.D., An Improved Sump Drain-Irrigation Device of Simple Construction, Archives of Surgery New York, pp. 511-513, 1972 vol. 105.
Wu, W.S., et al. Vacuum therapy as an intermediate phase in wound closure: a clinical experience, Eur J Past Surg (2000) 23: 174-177.
Davydov, Y. A. et al., "The Bacteriological & Cytological Assessment of Vacuum Therapy of Purulent Wounds", Vestnik Chirurgia 1988, Oct. Edition 1987, pp. 48-52.
International Preliminary Report on Patentability, re PCT Application No. PCT/GB2012/000489, dated Dec. 27, 2013.
Saxena, V., "Genomic Response, Bioinformatics, and Mechanics of the Effects of Forces on Tissues and Wound Healing" S.M., Mechanical Engineering, Massachusetts Institute of Technology, 2001, 1-167.
Definition of "3D Printer", American Heritage Dictionary of the English Language, Fifth Edition, 2016, accessed Feb. 22, 2018, in 1 page. URL: https://www.thefreedictionary.co.

\* cited by examiner

WOUND CONTACTING MEMBERS AND METHODS

CROSS-REFERENCE TO RELATED APPLICATIONS

This application is a U.S. National Phase of the PCT International Application No. PCT/GB2012/000489, filed on Jun. 7, 2012, and which claims priority to UK Application Nos. 1109497.6, 1109500.7, and 1109502.3, all filed on Jun. 7, 2011.

FIELD OF THE INVENTION

Embodiments of the present invention relate to wound contacting members and methods, apparatuses, systems and kits incorporating the same. In particular, but not exclusively, embodiments relate to foam for preventing or inhibiting tissue in-growth and/or improving tissue granulation growth, a wound filler configured to prevent or inhibit tissue in-growth and/or improve tissue granulation growth, a method of treating a wound to prevent or inhibit tissue in-growth and/or improve tissue granulation growth, and apparatus for treating a wound. The wound contacting members of the some embodiments may be used in negative pressure wound therapy (NPWT) applications. Certain embodiments relate generally to the treatment of wounds using NPWT, and more specifically to an improved apparatus and method thereof.

BACKGROUND OF THE INVENTION

NPWT, often referred to as topical negative pressure (TNP) or vacuum assisted closure, has been shown to be extremely useful in the treatment of many wound types including but not limited to chronic, complex acute wounds by making the healing thereof faster and more controlled. Further, NPWT has been shown to be useful in the treatment of burns, flaps, grafts and incisional wounds. It is to be understood that the term wound may have a broad interpretation and may include damage to or loss of soft tissue in a mammalian body. The apparatus used for applying NPWT generally includes a drape or sealing film or similar to create a closed environment over the wound. An aspirant conduit is brought into fluid communication with the closed environment and connected at a distal end to a vacuum source, such as an electrically driven pump or manual pump for example, to create a negative (reduced) pressure within the wound cavity compared to ambient pressure. The reduced pressure causes many beneficial therapeutic effects to the wound such as increased blood flow, faster growth of granulation tissue, and removal of exudates away from the wound, for example.

NPWT can be used to treat wounds of many shapes and sizes. The wounds may also have significant depth and therefore significant volume. Clinicians continue to require enhanced outcomes from the modern NPWT dressing. In particular, large wounds where considerable tissue loss has been experienced by the patient often require rapid growth of (tissue before closure can take place. In such cases rapid formation of granulation tissue is desirable in order to fill the defect in the tissue and promote wound contraction and finally re-epithelialization.

Preferably wounds should heal from the base up, and close in from the edges, desirably in a uniform manner. In particular it is desirable that the wound does not close over and form an occluded cavity or 'dead space' in the tissue, as such a cavity would be vulnerable to infection.

To prevent the formation of occluded cavities during NPWT, the wound may be packed with a filler that desirably has some resilience to resist the compressive forces created during NPWT, yet allows transmission of negative pressure and fluid flow. A purpose of the filler is to keep the edges of the wound apart so that they cannot grow over and form such cavity. When negative pressure is applied to a wound site, there is a tendency for the filler to collapse and be pushed towards the wound bed. The filler may be shaped by the clinician to fit the particular wound and placed in the wound to form intimate contact with the wound bed.

The filler may also provide fluid flow channels in order to provide a uniform reduced pressure distribution over the surface area of the wound and to promote efficient aspiration of fluid exudates away from the wound surface (generally into a remote waste receptacle associated with the aspirant conduit or into a storage area within the wound dressing itself). The presence of a wound filler may also stimulate growth of new tissue by subjecting the underlying tissue to a degree of stress. It is well known that application of stress to the cells in the wound resulting from the topography of the wound filler imparting strain on the wound surface is an important factor in stimulating cell proliferation and increasing the production of extracellular matrix. It has been shown that by increasing tissue strain and thus increasing cell stress, proliferation of cells can be increased.

Known wound fillers often consist of open-celled foam, such as reticulated foam, or gauze. Both these types of filler allow good transmission of negative pressure and allow fluid removal, yet suffer from various drawbacks. Foam fillers often suffer from the fact that tissue can grow into the foam structure. The foam may become stuck to the wound bed, making the filler difficult to remove when changing the dressing. Newly formed granulation tissue may be torn away with the foam when the filler is removed, which may cause patient pain during removal of the filler. This can be traumatic to the wound and to the patient. The clinician is often faced with having to compromise between changing a dressing early to keep tissue in-growth to a minimum and leaving the dressing in place to minimize nursing time, treatment cost and patient access. This is a particular problem with current open pore foam fillers (i.e. foam having a very open pore structure). Thus use of open pore wound fillers tends to be limited to 2 to 3 days, beyond which significant tissue in-growth and subsequent attachment is thought to occur, at least potentially resulting in damage to the tissue and pain on removal. Gauze fillers and mixed open-cell/closed-cell foam fillers (e.g. poly vinyl alcohol based foam) generally perform better with respect to in-growth, but may be inferior in their ability to induce comparable levels of observed granulation tissue. It is well known that the inclusion of a wound contact layer located between the filler and the wound surface reduces the chance of tissue growing into the foam, although again this is to the detriment of reducing the observed granulation tissue formation. Healing time may also be lengthened as a result. In many circumstances a wound contact layer is the term given to a thin sheet or membrane of material that may be positioned directly onto a wound bed. However, a wound contact layer could be any layer or member that contacts a wound bed.

A number of attempts have been described in the prior art to limit tissue in-growth into a filler. However, this has always been at the expense of limiting granulation tissue growth and thus overall clinical efficacy. U.S. Pat. No.

6,695,823, US2007/0293830, US2008/091521, US2006/046060, US2008/0317826, US2009/0105671, US2008/0300555, WO2008/141228, US2010/0160876 and WO02009/089016 describe such attempts.

SUMMARY

It is an aim of embodiments of the present invention to at least partly mitigate the above-mentioned problems.

It is an aim of embodiments of the present invention to provide improved wound contacting materials compared to known materials.

It is an aim of embodiments of the present invention to provide apparatus and methods for preventing, minimizing, delaying, reducing or inhibiting tissue in-growth.

It is an aim of embodiments of the present invention to provide a wound filler or wound contacting member that reduces in-growth whilst also promoting the formation of granulation tissue.

According to a first aspect of the present invention there is provided a wound contacting member for negative pressure wound therapy (NPWT), comprising a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

According to a second aspect of the present invention there is provided a wound contacting member for negative pressure wound therapy (NPWT), comprising a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

According to a third aspect of the present invention there is provided a wound contacting member for negative pressure wound therapy (NPWT), comprising a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

According to a fourth aspect of the present invention there is provided apparatus for the treatment of wounds in a human or animal subject by negative pressure wound therapy (NPWT), comprising:
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

According to a fifth aspect of the present invention there is provided apparatus for the treatment of wounds in a human or animal subject by negative pressure wound therapy (NPWT), comprising:
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

According to a sixth aspect of the present invention there is provided apparatus for the treatment of wounds in a human or animal subject by negative pressure wound therapy (NPWT), comprising:
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

According to a seventh aspect of the present invention there is provided a kit for use in negative pressure wound therapy (NPWT), comprising
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

According to a eighth aspect of the present invention there is provided a kit for use in negative pressure wound therapy (NPWT), comprising
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

According to a ninth aspect of the present invention there is provided a kit for use in negative pressure wound therapy (NPWT), comprising
    a wound contacting member for applying to a wound bed;
    a cover member configured to form a sealed enclosure around the wound contacting member when the wound contacting member is applied to the wound bed,
    wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

According to a tenth aspect of the present invention there is provided a method of treating a wound in a human or animal subject, comprising:
    applying a wound contacting member to a wound bed, wherein
    the wound contacting member comprises a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

According to a eleventh aspect of the present invention there is provided a method of treating a wound in a human or animal subject, comprising:
    applying a wound contacting member to a wound bed, wherein
    the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

According to a twelfth aspect of the present invention there is provided a method of treating a wound in a human or animal subject, comprising:
    applying a wound contacting member to a wound bed, wherein
    the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

According to a thirteenth aspect of the present invention there is provided a wound contacting member for negative pressure wound therapy (NPWT) selected to reduce pain upon removal from a wound, the wound contacting member comprising a network of strut elements separated by pores, wherein the wound contacting member comprises at least one attribute selected from the group consisting of:
    at least 95% of the strut elements having a thickness of between 0.007 and 0.5 mm, and
    one or more strut element having a thickness of 0.23 mm or more, as measured by micro-CT.

The wound contacting element according to this thirteenth aspect may further comprise both at least 95% of the strut elements having a thickness of between 0.007 and 0.5 mm, and one or more strut element having a thickness of 0.23 mm or more, as measured by micro-CT. The wound contacting element may optionally further comprise one or more of the following attributes:
    at least 90% of the pores having a diameter of between 2.3 and 5.5 mm;
    at least 95% of the pores having a diameter of 2.5 mm or greater;
    the most frequent pore size is between 3.3 and 4.7 mm;
    a pore size of between 5 and 25 ppi;
    at least 10% of the strut elements having a thickness of 0.23 mm or more;
    a compressive strain at −120 mmHg of between about 50 and about 90%;
    a compressive strain at −120 mmHg of between about 50 and about 80%;
    a compressive strain at −120 mmHg of between about 55 and about 75%;
    a total surface area of between 30 and 150 mm$^2$ in a 126 mm$^3$ volume, as measured by micro-CT;
    a total surface area of between 45 and 100 mm$^2$ in a 126 mm$^3$ volume, as measured by micro-CT; and/or
    a total surface area of between 55 and 95 mm$^2$ in a 126 mm$^3$ volume, as measured by micro-CT.

The wound contacting member may further promote granulation tissue growth at a wound bed simultaneously with the prevention or reduction of tissue in-growth into the wound contacting member. The wound contacting member may be foam, which may be reticulated, polyurethane, and/or polyether polyurethane. The wound contacting member may have a density between 0.03 and 0.04 g·cm$^{-3}$.

According to a fourteenth aspect of the present invention there is provided an apparatus for the treatment of wounds in a human or animal subject by negative pressure wound therapy (NPWT), comprising a wound contacting member of the thirteenth aspect, and a cover member configured to form a sealed enclosure around the wound contacting member when the wound contacting member is applied to the wound bed. The apparatus may further comprise a connection device for placing the enclosure in fluid communication with a vacuum source.

According to a fifteenth aspect of the present invention there is provided a method for treating a wound, comprising applying a wound contacting member of the thirteenth aspect to a wound bed. The method may further comprise the step of applying a cover over the wound contacting member to form a sealed enclosure, and/or the step of applying negative pressure wound therapy (NPWT) to the wound bed. The method may be used to promote granulation tissue growth at the wound bed simultaneously with preventing or reducing tissue in-growth into the wound contacting member. The method may apply negative pressure to the wound for at least 72 hours in the range of −40 mmHg to −200 mmHg, the negative pressure and the wound contacting member promoting the growth of granulation tissue at the wound, wherein the negative pressure causes the wound contacting member to compress to decrease the void volume and increase the strut volume. The method may further comprise removing the cover and the wound contacting member from the wound, wherein the force required to remove the wound contacting member from the wound is less than 5 mN. In some embodiments, the application of negative pressure to the wound causes the wound contacting member to indent into tissue of the wound by about 950 to about 1000 μm. In some embodiments, prior to the step of applying negative pressure, the wound contacting member has a pore volume of about 90 to about 98% of the total volume, and after the step of applying negative pressure for at least 72 hours, the wound contacting member has a pore volume of about 70 to about 90% of the total volume.

Certain embodiments provide the advantage that in-growth of tissue to a wound contacting member or filler within a conventional time period (such as 3 days) is completely or substantially prevented. Removal of a wound contacting member from the wound site is therefore less painful for the patient, and less damaging to the tissue at the wound site compared to known materials. Certain embodiments provide the advantage that an advantageous degree of granulation tissue is stimulated by the presence of the wound contacting member. This enables a faster healing process to be accomplished at the wound compared to known methods and apparatus. Certain embodiments provide an improved wound treatment apparatus and method for NPWT (for example at pressure of between 40 and 200 mmHg below atmospheric).

BRIEF DESCRIPTION OF THE DRAWINGS

Embodiments of the invention are further described hereinafter with reference to the accompanying drawings, in which.

In the drawings like reference numerals refer to like parts.

DETAILED DESCRIPTION

Figure 1:
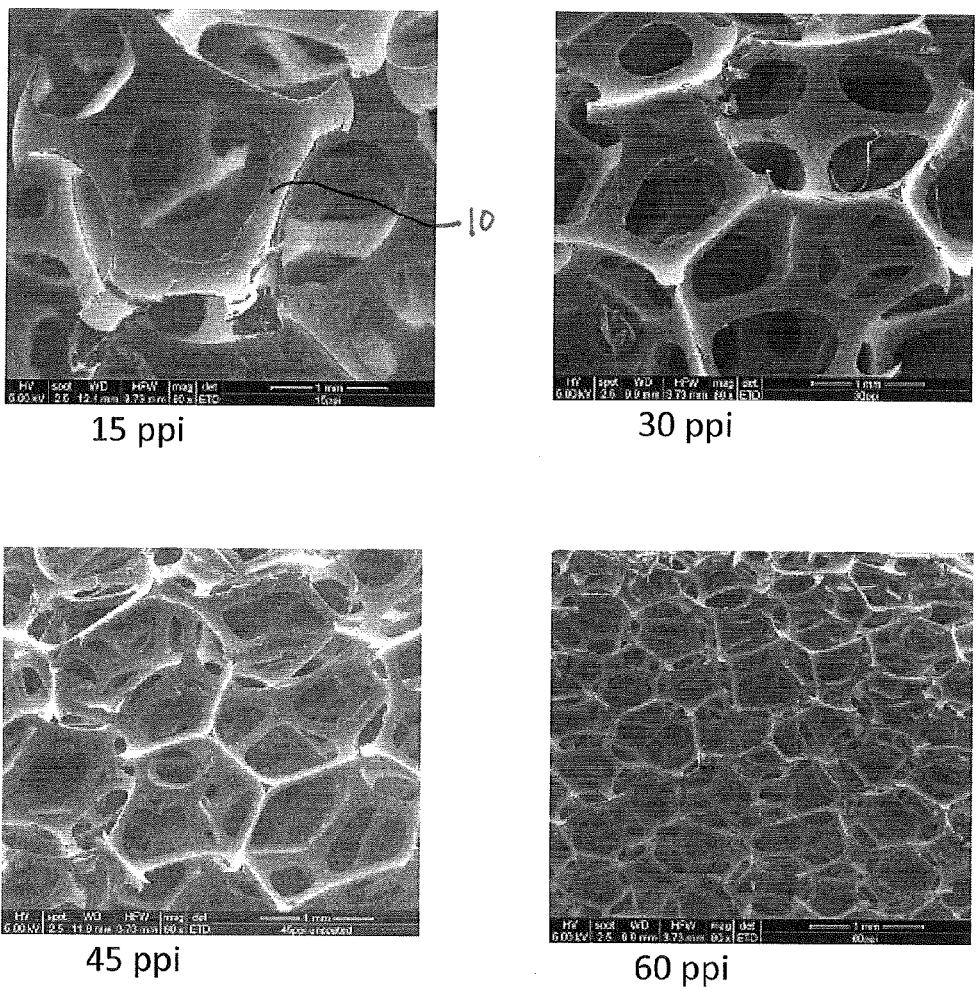
FIG. 1 shows Scanning Electron Microscope images of foams having different pore sizes.

The terms wound contacting member, wound packer material and wound filler are herein used synonymously to refer to any suitable component used to contact with and/or at least partly fill a wound, such as foam, gauze or other material. The term wound contact element is used to refer to individual portions of a wound filler that are capable of actually contacting with a wound bed.

As used herein, the term in-growth is used in the more usually recognised manner, i.e. to refer to the formation of tissue that grows at least part way into the pores or cavities of a wound filler, and encompasses structural elements of the wound filler at least partially, possibly attaching to the wound filler. That is, the tissue becomes at least partly entangled with the wound filler by growing within the wound filler, and partially enveloping the filler, and possibly attaching to the filler material, such that removal of the filler from the tissue becomes difficult or painful to the patient. In other words, tissue grows to an extent that it at least partially anchors to or around elements of the wound filler. A point at which tissue is anchored to a wound filler may be termed an anchor point.

Granulation tissue refers to the newly growing tissue material at a wound site formed to heal the wound. The tissue is perfused, fibrous connective tissue including a variety of cell types. The tissue will grow generally from the base of the wound to gradually fill the entire wound space.

Foam is a substance formed by trapping gaseous bubbles in a solid. As described above, foams may have very different structures, from a closed cell structure, with no interconnected gas bubbles (known as pores, i.e. each pore being completely enclosed and surrounded by material), to varying degrees of an open cell structure having connected pores and a three-dimensional network structure or 'tessellation' of material supporting the pores (the tessellation not necessarily being regular). Many variations of cell structure are possible, with different pore size, different ratios of gas to surrounding material, etc. The surrounding tessellations of material may be formed in different structures, and each individual section of a tessellation may be referred to as a strut. A typical strut is identified in FIG. 1 by reference number 10. The face of the foam in contact with the wound therefore comprises spaced apart wound contact elements each having a wound contact surface. Pores formed by bubbles often tend to form as generally spherical apertures, and the struts often tend to take a rod-like shape having relatively thicker ends and a relatively narrower central portion, and with a triangular-like cross-section.

As used herein, ppi (pores per inch) is used as a measure of the number of pores over a 1 inch (2.54 cm) straight line of a foam material. A person skilled in the art will understand that pore size of a standard foam material is specified by manufacturers in industry and has a certain degree of consistency.

The present inventors have conducted an in-depth study into various types of foam for use in contacting a wound bed, and the various parameters associated with such foams. Surprisingly, it has been found that in one embodiment, foams in which at least 90% of the pores have a diameter of between 2.3 and 5.5 mm, and at least 90% of the pores have a diameter of 2.5 mm or greater, and at least 95% of the struts have a thickness of between 0.007 and 0.5 mm, and the foam includes one or more strut having a thickness of 0.23 mm or more, as measured by micro-CT, work particularly well at both enhancing granulation tissue growth and preventing or reducing in-growth compared to commonly used foams or fillers in NPWT.

Additionally, it has also been found that in other embodiments foams in which at least 95% of the strut elements have a thickness of between 0.007 and 0.5 mm, and one or more strut element having a thickness of 0.23 mm or more, as measured by micro-CT, and the foam having a compressive strain at −120 mmHg of between about 50 and about 90%, surprisingly work particularly well at both enhancing granulation tissue growth and preventing or reducing in-growth compared to commonly used foams or fillers in NPWT.

Last, it has also surprisingly been found that in other embodiments foams in which at least 95% of the strut elements have a thickness of between 0.007 and 0.5 mm, and one or more strut element having a thickness of 0.23 mm or more, and the strut elements have a total surface area of between 30 and 150 mm$^2$ in a 126 mm$^3$ volume, as measured by micro-CT, also work particularly well at both enhancing granulation tissue growth and preventing or reducing in-growth compared to commonly used foams or fillers in NPWT.

Other embodiments comprise foams having only one, a combination of two, three, four, five or all six of the following properties: (1) at least 90% of the pores have a diameter of between 2.3 and 5.5 mm, (2) at least 90% of the pores have a diameter of 2.5 mm or greater, (3) at least 95% of the struts have a thickness of between 0.007 and 0.5 mm, (4) the foam includes one or more strut having a thickness of 0.23 mm or more, as measured by micro-CT, (5) the foam having a compressive strain at −120 mmHg of between about 50 and about 90%, and/or (6) the strut elements have a total surface area of between 30 and 150 mm$^2$ in a 126 mm$^3$ volume, as measured by micro-CT. Further embodiments of desirable foams are described below.

Despite previous studies indicating that there is always some payoff between tissue granulation growth and in-growth, the present inventors have surprisingly found a range of foam parameters in which both the tissue granulation growth can be good (i.e. high) and the degree of in-growth can be considered good (i.e. low or absent).

It was previously thought that greater granulation tissue formation was associated with greater attachment of tissue in a wound filler, and that the degree of in-growth to a foam increases as the pore size increases (e.g. smaller pore size foam such as 60 ppi result in low in-growth whereas larger pore size foams such as 30 ppi result in larger degrees of in-growth). However, contrary to this expected result, foams with pore size equating to a pore count of less than 25 ppi (i.e. around 5 to 25 ppi) were shown by the present inventors to provide excellent stimulation of granulation tissue and no apparent in-growth, requiring minimal force to remove the filler from the wound, leading to low disruption of the wound bed upon removal. In particular, foams with a pore count of 5 to 25 ppi, and particularly 10 to 20 ppi, and more particularly 15 ppi, were found to be suitable wound contacting members giving the advantages described herein. These advantages have been shown primarily in relation to wound treatment under NPWT.

It is believed that when at least 95% of the strut elements have a thickness of between 0.007 and 0.5 mm, and the wound contacting member includes one or more strut element having a thickness of 0.23 mm or more, as measured by micro-CT, this contributes to the surprising effects on tissue growth and related properties noted herein.

Embodiments of the present invention have provided surprising new advantages compared to known apparatus and methods, and new technical effects in the improvement of granulation growth and in-growth as described herein.

The foams of the present disclosure are highly suitable as a wound filler or other wound contacting member. Use of the foam could significantly improve the overall dressing removal experience for patients and clinicians. This could also increase the dressing wear time and lead to reduced costs. It has been found that surprisingly, granulation tissue formation does not have to be synonymous with in-growth as previously thought. A person skilled in the art will realise that with the certain embodiments, different foam materials could be used to provide the desired effect.

When using the wound, contacting member of the present disclosure, NPWT can be applied to a wound by creating a closed environment over the wound. The apparatus includes a drape or sealing film or similar. An aspirant conduit is brought into fluid communication with the closed environment and connected at a distal end to a vacuum source, such as an electrically driven pump or manual pump for example, to create a negative (reduced) pressure within the wound cavity compared to ambient pressure. A deep wound may be packed with a wound packer or wound filler.

Figure 2:
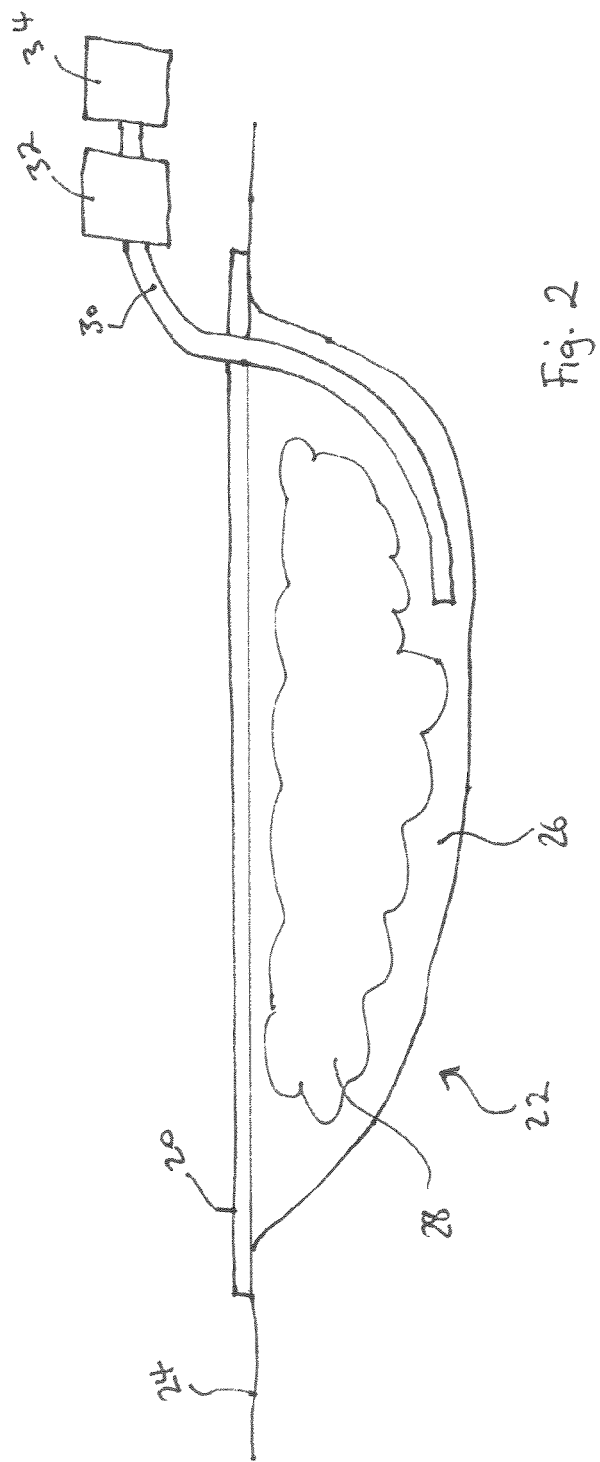
FIG. 2 illustrates NPWT apparatus.

FIG. 2 illustrates a generalized view of an embodiment of a NPWT apparatus. FIG. 2 illustrates a view of a drape 20 which, in use, is located over and around a wound site 22. The drape 20 acts as a dressing covering the wound and may be any type of dressing normally employed with NPWT and, in very general terms, may comprise, for example a semi-permeable flexible, self-adhesive drape material as is known in the dressings art to cover the wound and seal with surrounding sound tissue 24 to create a sealed cavity or void over the wound. This sealed cavity or void is referred to hereinafter as a wound chamber 26. Hereinafter a chamber is taken to mean an enclosed volume of any geometry. The chamber may be of fixed or flexible geometry.

As illustrated in FIG. 2 wound packer material or filler 28 may be used in the cavity between a wound bed and the drape. This helps to obtain an even vacuum distribution to be achieved over the area of the wound, amongst other functions.

An aspiration conduit (suction tube) 30 may be a plain flexible tube, for example, having a single lumen therethrough and made from a plastics material compatible with raw tissue. However, the aspiration conduit may alternatively have a plurality of lumens therethrough to achieve specific objectives. In the example shown, the suction tube is connected from the wound chamber in turn to a waste collection canister 32 for collecting exudates from the wound site, and then to a pump for applying the negative pressure. From the exit port of the waste canister to the final exhaust port of the pump, the fluid is substantially gaseous only. The waste canister 32 may be provided with one or more filters (not shown) which prevent the escape via an exit port of liquid and bacteria from the waste canister. For example, the filters may comprise a 1 μm hydrophobic liquid filter and a 0.2 μm bacteria filter such that all liquid and bacteria is confined to an interior waste collecting volume of the waste canister 32. The pump may further be provided with a silencer system (not shown) and/or a final filter having an activated charcoal matrix which ensures that no odours escape with the gas exhausted from the pump via an exhaust port.

Thus, in use, the drape 20 is positioned over a wound site, fluidly connected to the pump, and negative pressure applied. As the pump is activated, a negative pressure is created in the aspiration tube 30 and communicated to the wound chamber 26. Treatment may continue as long as necessary, intermittently or constantly.

It is envisaged that the negative pressure range for the apparatus may be between about −40 mmHg and about −200 mmHg (note that these pressures are relative to normal ambient atmospheric pressure thus, −200 mmHg would be around 560 mmHg in practical terms). Aptly, the pressure range may be between about −75 mmHg and about −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg. Aptly the pressure of the wound chamber is between −125 mmHg and −20 mmHg.

Although NPWT is a beneficial system with which certain embodiments described herein can be employed, other arrangements can be envisaged without the use of negative pressure. For example, for less deep wounds, a dressing may be applied including the above-described foam as a kind of wound contact layer, and a cover layer stretched over the wound contact layer so as to apply some positive pressure to the wound contact layer and the wound.

Figure 3:
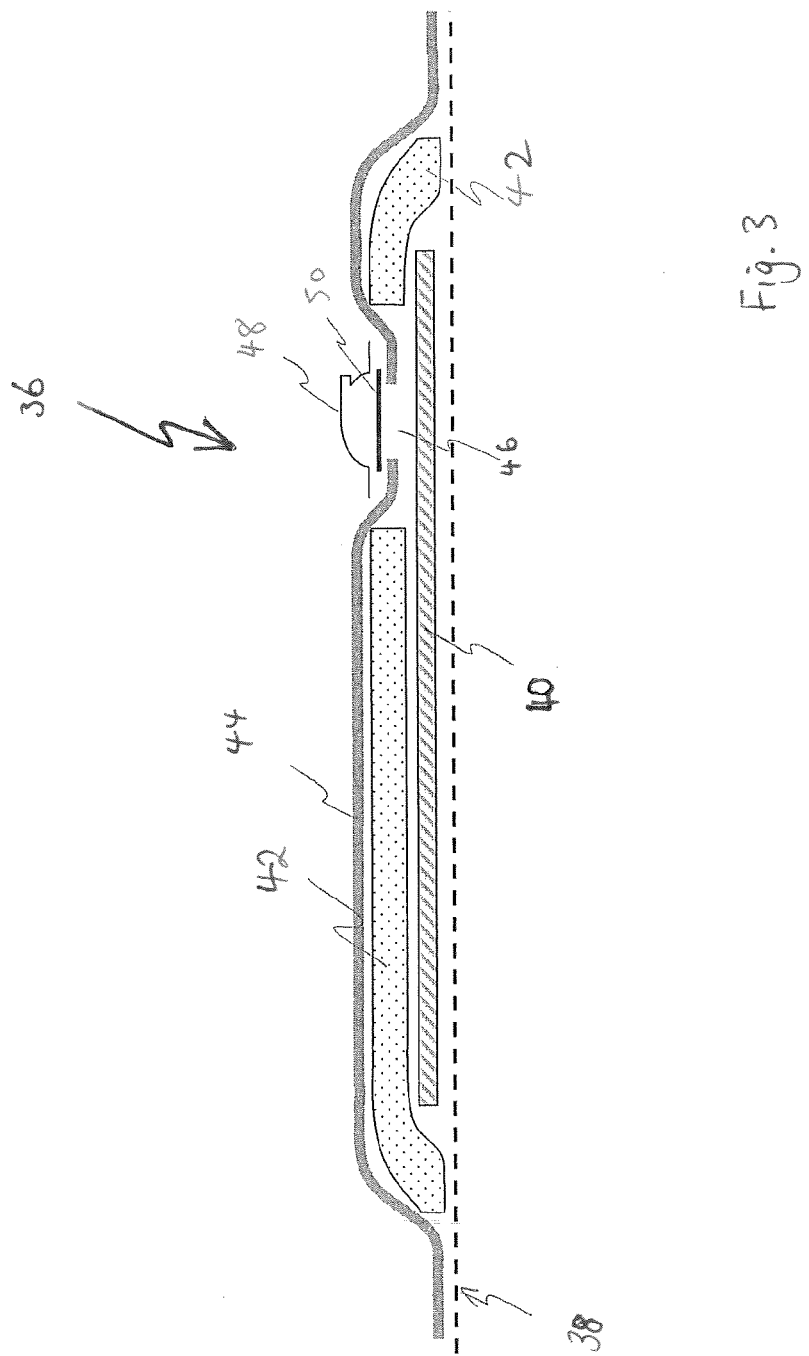
FIG. 3 illustrates an alternative NPWT apparatus.

As shown in FIG. 3, in some embodiments a wound dressing may be provided in which the dressing itself includes a storage area to contain exudates removed from the wound bed, rather than the separate canister described above. For example, the dressing 36 may include a layer 38 of wound contacting member. A layer of porous material 40, or transmission layer, allows transmission of fluid including liquid and gas away from the wound site into upper layers of the dressing. This layer remains open during NPWT, so that negative pressure can be communicated, and negative pressure is equalized over the wound site. A layer of absorbent material 42 of foam or non-woven or synthetic material and optionally superabsorbent material forms a reservoir for fluids removed from the wound site. A gas impermeable, moisture vapour permeable, cover layer 44 extends across the width of the dressing. The cover layer is sealed to the layer 38 in a border region around the circumference of the dressing. An orifice 46 is provided in the cover layer 44 to allow negative pressure to be applied to the dressing. A suction port 48 is sealed to the top of the cover layer over the orifice and communicates, negative pressure through the orifice. Tubing may couple the port to a suction pump (not shown). A filter element 50 that is impermeable to liquids but permeable to gasses is provided to act as a liquid barrier, ensuring no liquids escape from the wound dressing. Further details of such a wound dressing and associated devices and methods are found in U.S. Publication No. 2011/0282309 A1, the entirety of which is hereby incorporated by reference.

As such, a wound contacting member for negative pressure wound therapy (NPWT) of one embodiment is provided, comprising a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

Another wound contacting member for negative pressure wound therapy (NPWT) is provided, comprising a network of strut elements separated by pores, wherein at least 95% of the strut elements have a thickness of between 0.007 and 0.5 mm, and the wound contacting member comprises one or more strut-element having a thickness of 0.23 mm or more, as measured by micro-CT, and the wound contacting member has a compressive strain at −120 mmHg of between about 50 and about 90%.

Yet another wound contacting member for negative pressure wound therapy (NPWT) is provided, comprising a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 $mm^2$ in a 126 $mm^3$ volume, as measured by micro-CT.

In any of the embodiment described herein, at least 10% of the struts may have a thickness of 0.23 mm or more, as measured by micro-CT.

In any of the embodiments described herein, at least 90% of the pores may have a diameter between 2.3 and 5.5 mm. More aptly at least 95% have this diameter.

In any of the embodiments described herein, the member may have a compressive strain at −120 mmHg of between 50 to 80%, 50 to 90%, and more aptly between 55 and 75%.

In any of the embodiments described herein, the member may have a surface area of between 30 to 150 $mm^2$ in a 126 $mm^3$ volume. More aptly, the member has a surface area of between 45 to 100 $mm^2$ in a 126 $mm^3$ volume, and even more aptly between 50 and 95 $mm^2$.

In any of the embodiments described herein the material may be a foam, particularly reticulated foam. An embodiment of an apparatus suitable for treating wounds in a human or animal subject by NPWT may include a wound contacting member as described above, and a cover member.

Factors associated with foam pore size include void volume, strut size, strut thickness, material composition, material compressibility, anisotropy of pore dimensions, total surface area of material, and foam density.

It has been confirmed that differences in pore size of foam material can influence the degree of both tissue in-growth and granulation tissue growth.

Pore size of a foam can be related to the strut width (and strut strength—which may depend on density of the strut material). Without wishing to be bound by theory, it is believed that the pore size and strut width affect the extent or degree of indentation of a foam into tissue of a wound bed. It is further believed that indentation of foam into a tissue affects the stress on the tissue and strain within the tissue. For example, when a foam filler is applied to a wound using a NPWT apparatus, the foam struts push down on the wound surface during compression, while reduced pressure acts to urge the wound surface into the pores between the struts. This simultaneous pushing and pulling may result in strain known as 'microdeformational strain'. It is yet further believed that stress and strain received by a tissue affects the production of granulation tissue; and cell infiltration of leukocytes and tissue reorganisation are recognised as early indicators of the occurrence of granulation tissue formation.

In addition, stiffness and compressibility of a foam material will also affect the extent or degree of indentation of the foam into tissue.

Thus it is recognised that micro-deformational strain from foam struts contacting and exerting an amount of stress on a wound bed helps to promote granulation tissue growth and thus rapid healing.

Without wishing to be bound by theory, it is believed that in-growth of a tissue into a foam may be affected by one or more of pore size, strut size, strut surface area, and compressibility of the foam. The pore size may be affected by compressibility of the material of the foam (with a greater compressibility when subjected to negative pressure effectively reducing pore size and increasing strut surface area of the foam contacting the wound). The larger strut size (width) and thus greater wound contact area is thought to physically block tissue in-growth into a foam. A larger strut can limit the ability of tissue to grow into and around the foam sufficiently to block attachment of tissue within the foam. The strut surface area may be affected by compressibility of the material of the foam when subjected to negative pressure (with a greater compressibility effectively reducing pore size and increasing strut surface area of the foam contacting the wound). The compressibility of the material may affect the pore size (with a greater compressibility when subjected to negative pressure effectively reducing pore size and increasing strut surface area of the foam contacting the wound).

It is realised that application of negative pressure will affect the characteristics of the foam. That is, on application of negative pressure to a foam the percentage void volume will decrease, the percentage strut volume and surface area will both increase, the pore size will decrease and the pore shape will change (increasing anisotropy).

Suitable foams for use may include polyurethane (such as polyester urethane and polyether urethane), polyolefins (such as polyethylene), polyvinyl alcohol, silicone, hydrocortisone acetate, ethylene vinyl acetate, cellulose, cellulose acetate, and blends thereof such as polyester-silicone for example.

Vishal Saxena et al (Journal of Plastic & Reconstructive Surgery, Vol. 114, No. 5, 1086-1096) describe the use of computer simulations of various porous wound fillers and their effects on the tissue strain of the wound bed.

Without wishing to be bound by theory, it is believed that the relatively larger pore size of foams according to embodiments of the present disclosure allows a relatively larger space for underlying tissue to grow into. However, because of the strut presence between the pore area, the struts can indent to a significant depth into the tissue, causing a large degree of micro-strain and therefore promoting a high amount of granulation tissue growth formation. Because the struts are large and the intervening space capacity is large (i.e. at the given density of material), tissue is inhibited or slowed from growing over the top of the struts into the adjacent structure of the foam.

It was noted during experimentation that a large difference in surface area existed between foams having a pore count of 30 ppi or more, and those having a pore count of less than 30 ppi (at similar density). It is thought that whilst foams having 5 to 25 ppi encourage granulation tissue, the noticeably lower surface area helps to avoid tissue growing into and attaching to the foam. In general, it has previously been thought that with a very small pore size, tissue in-growth is low, because there is less granulation tissue growth, and that as pore size increases, granulation tissue growth increases, as does in-growth. However, the inventors have found that foams having 5 to 25 ppi in one embodiment of the invention have little in-growth. In other embodiments, foams having the strut properties described above have little in-growth.

With certain embodiments, wound contact elements are spaced so as to promote granulation tissue growth, and yet have sufficient spacing (and/or depth) to prevent tissue in-growth.

Formation of granulation tissue is promoted in locations adjacent wound contact elements. In accordance with embodiments of the present disclosure, coalescence between such locations of tissue may be prevented or inhibited by the particular choice of wound contact element spacing and/or the pore depth.

Figure 4:
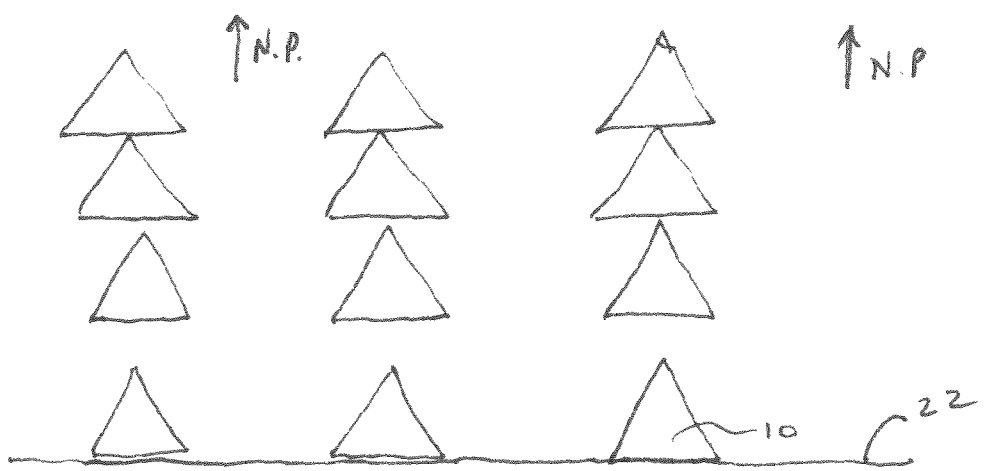
FIG. 4 illustrates a foam contacting a wound site under compression from negative pressure.

Typically foam compression under NPWT treatment is observed to be not evenly distributed over the volume of a foam. Often compression of pores and struts become gradually greater in a direction away from the wound bed. A schematic illustration of the compression of foam under negative pressure is shown in FIG. 4. FIG. 4 only illustrates foam struts in cross section, as a simplistic illustration of the effect. It can be seen from FIG. 4 that under NPWT, (the direction of application identified generally by arrows N.P.), the foam tends to be more open along the edge of the foam that contacts the contact surface or wound bed.

Figure 5:
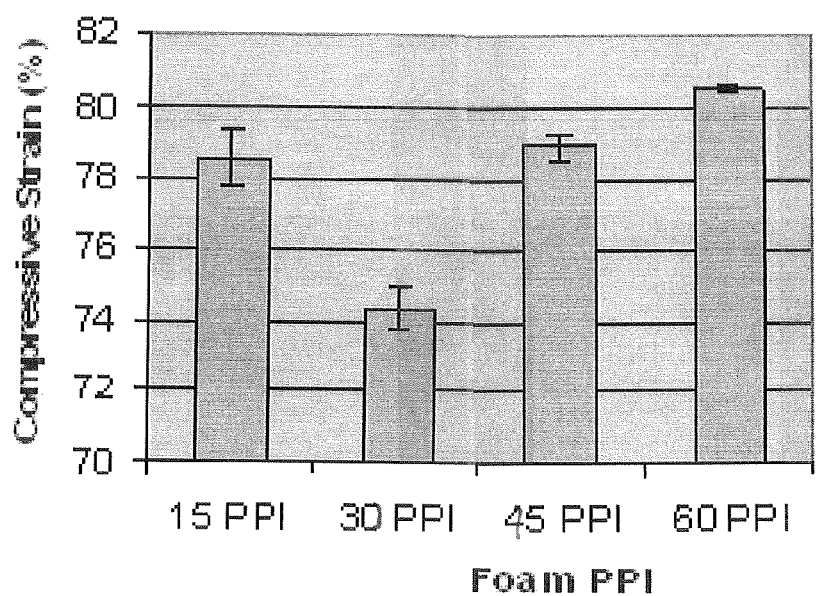
FIG. 5 is a graph of compressive strain measured for foams with different pore counts.

Furthermore, it was noted that foams with the above-mentioned suitable characteristics also created a 'buckling' effect when tested under negative pressure. The foam struts had dimensions that created a particularly slender strut form, and under negative pressure the struts on the edge of the foam facing the wound bed (the 'first layer' of struts) would function in the usual manner, contacting and applying stress to the tissue at the wound bed. Yet the struts behind that first layer of struts would buckle over, creating a kind of blanket effect behind the first layer of foam struts. A study checking the compressibility of the foams of different pore sizes confirmed that the foams with the above-mentioned suitable characteristics went against the trend of foams with larger pore sizes that had lower compressibility (see FIG. 5). Such a blanket formation may also lead to the physical blocking of tissue growing into the foam pores creating in-growth.

Experimental Data

The present inventors tested various parameters of foams having different ppi (pores per inch). The foam material was a standard open cell fully reticulated polyether polyurethane foam available from Acoustafoam Limited in Telford, Shropshire, UK. The chemical composition of each foam sample was confirmed to be the same as the other foams tested using infra-red spectroscopy.

Example 1

The inventors tested parameters of a number of foams having different pore counts including 15 ppi, 30 ppi, 45 ppi and 60 ppi foam. Results are shown in Table 1, below.

The inventors viewed the foams under stereomicroscope and scanning electron microscope (SEM). Images from the SEM study are shown in FIG. 1. The inventors also viewed the foams in a compressed state under SEM.

The inventors calculated foam density and foam 'openness' including the percentage of struts, surface area of the struts, percentage of pores, and anisotropy of the pore space, using the techniques described below under 'Measurement Techniques'. Specifically, all measurements other than average density were measured by micro-CT analysis as described below.

TABLE 1

| Parameter | 15 ppi | 30 ppi | 45 ppi | 60 ppi |
| --- | --- | --- | --- | --- |
| Average density (g · cm$^{-3}$) | 0.031 | 0.036 | 0.028 | 0.027 |
| % strut presence | 2.8 | 3.5 | 2.2 | 2.3 |
| Surface area of the struts (mm$^2$ in a 126 mm$^3$ volume) | 92 | 203 | 202 | 336 |
| % pores | 97.2 | 96.5 | 97.8 | 97.7 |
| Anisotropy of pore space | 1.20 | 1.32 | 1.24 | 1.24 |
| Strut width range (mm) | 0.007-0.617 | 0.007-0.256 | 0.007-0.173 | 0.007-0.104 |
| Modal Pore size (most frequent pore size) (mm) within the range | 3.338-3.440 | 1.797-1.900 | 1.144-1.185 | 0.645-0.686 |

Aptly, the wound contacting member has an average density of between about 0.002 and about 0.004 g·cm$^{-3}$.

Aptly, the wound contacting member has between about 2.5 and about 3% struts in the total volume.

Example 2

The inventors studied the effects of foams with different pore sizes under NPWT in an in-vivo porcine wound model. Wounds were created, a piece of foam was sutured to the wound for histological purposes, a further circular piece of foam of 6 cm diameter and 2 mm deep was added to the wound for pull-out force data purposes, and then the wound was treated with NPWT. Each wound was circular (i.e. having a circular wound base), 6 cm in diameter and 2 cm deep, reaching subcutaneous tissue.

Figure 6:
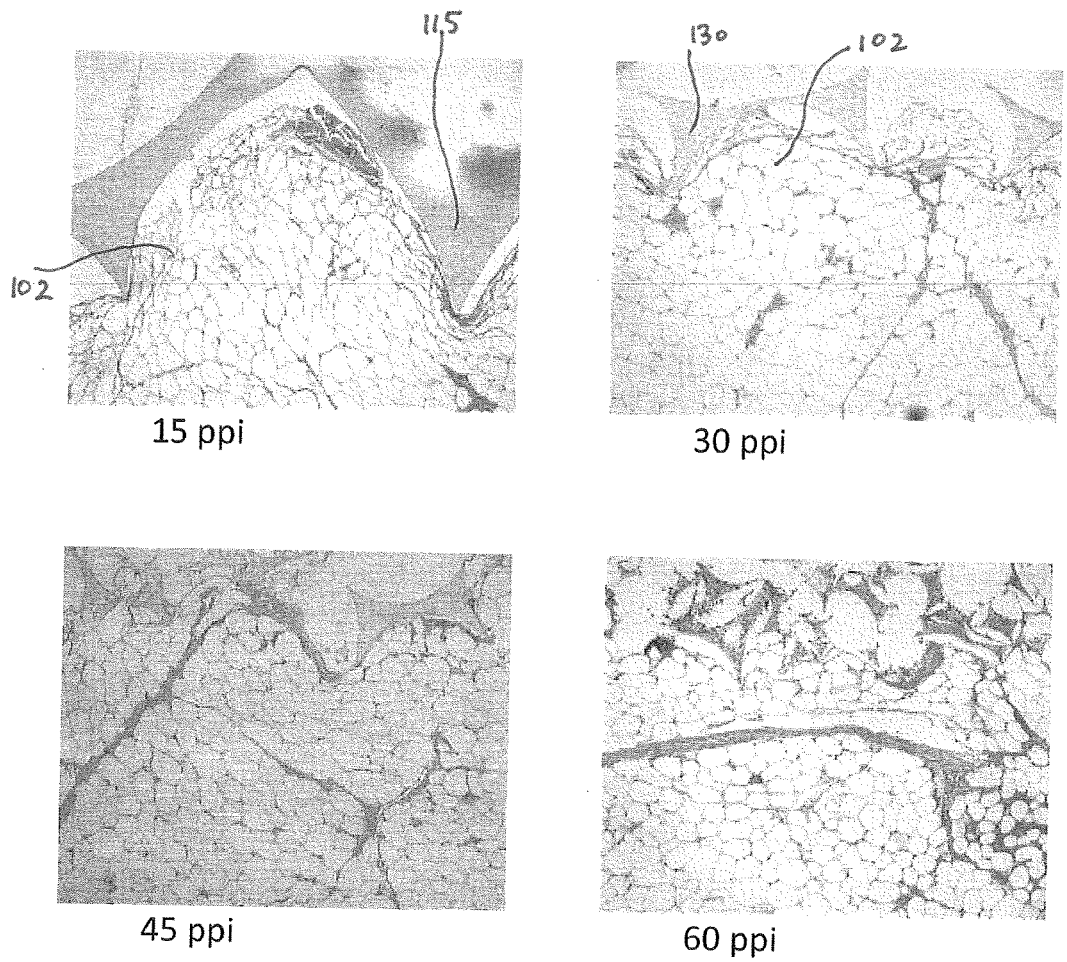
FIG. 6 shows images of foams contacting a wound bed after NPWT.

After 72 hours NPWT at −125 mmHg constant pressure, the foam and underlying wound bed were cut away and inspected histologically using light microscopy. Images of the results are shown in FIG. 6. As can be seen from FIG. 6, the indentation of the strut 115 of the 15 ppi foam into the tissue of the wound bed 102 is significantly greater than the indentation of the strut 130 of the 30 ppi foam.

Figure 7:
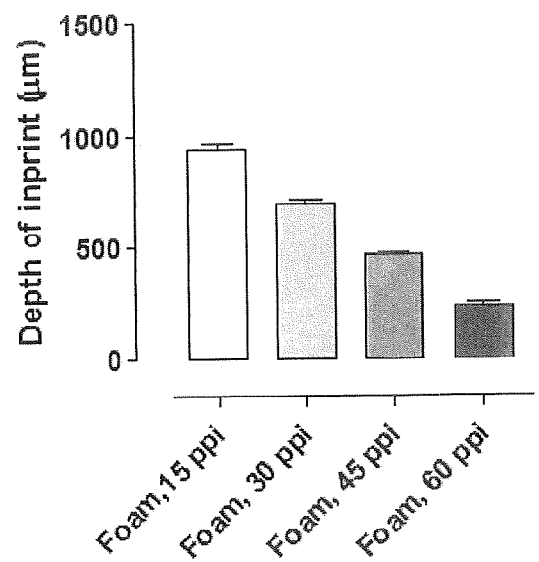
FIG. 7 is a graph of wound bed imprint depth of different foams after NPWT.

The average depth of imprint of the foam into the wound bed was also measured histologically. Tabulated results are shown in FIG. 7. It is clear that the foam with 15 ppi gave a significantly larger depth of imprint into the wound bed than any other sample. Aptly, the depth of imprint into a wound bed is between about 900 and about 1200 µm. More aptly, the depth of imprint is between about 900 and about 1000 µm.

Figure 8:
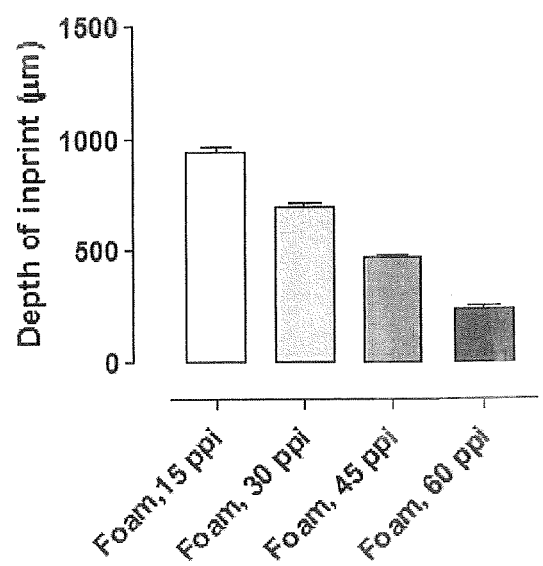
FIG. 8 is a graph of granulation tissue grades of different foams after NPWT.

The granulation tissue formed adjacent to the foam was also studied visually and graded on a scale of 0 to 5, 0 being a complete absence of newly formed granulation tissue and 5 being the strong presence of granulation tissue as observed by two independent clinicians. The 15 ppi foam gave the greatest level of observed granulation tissue formation compared to the other samples. Tabulated results are shown in FIG. 8. Again, as shown the 15 ppi foam scored the highest rating for degree of granulation tissue formation compared to the other foams.

Figure 9:
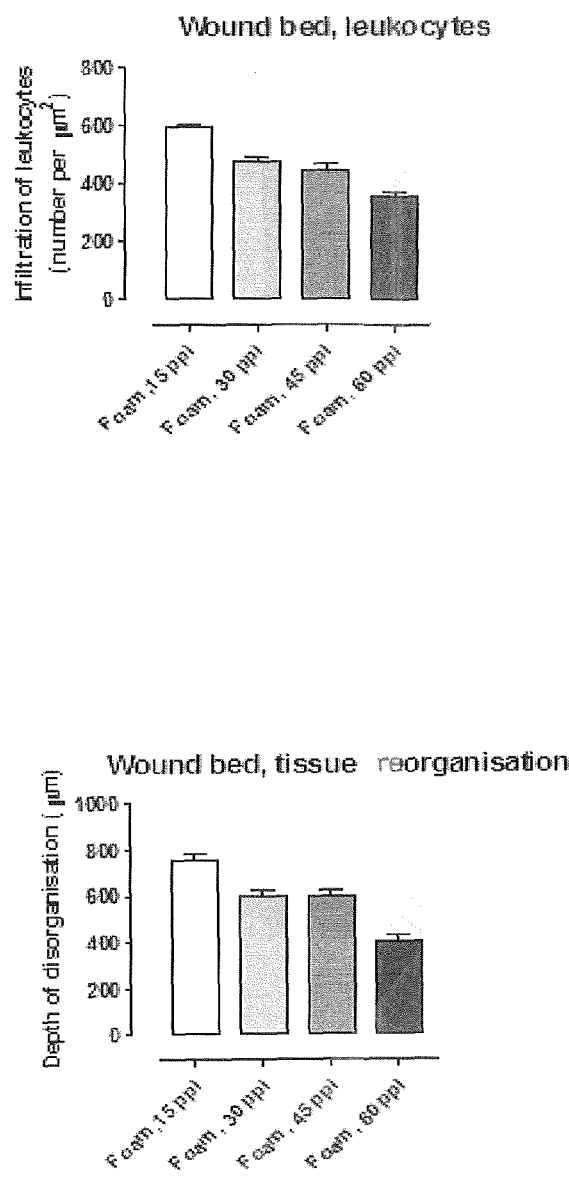
FIG. 9 shows graphs of various wound bed characteristics after NPWT.

In addition, early signs of granulation were noted. In particular, FIG. 9 shows graphs of the number of leukocytes (white blood cells involved in the early inflammatory phase of wound healing) present per $\mu m^2$ for the different pore counts of foam. The results are given for the foam present at the base of a wound. In addition, there is shown the degree of tissue reorganisation, measured by depth of reorganisation in µm, for the foam present at the base of a wound. It can be seen that the 15 ppi-foam leads to a higher infiltration of leukocytes over a given area as well as a greater degree of tissue reorganisation than the other foams tested. As such, the higher number of leukocytes present after using the 15 ppi foam indicates tissue granulation growth may be increased or faster compared to the other foams tested.

Figure 10:
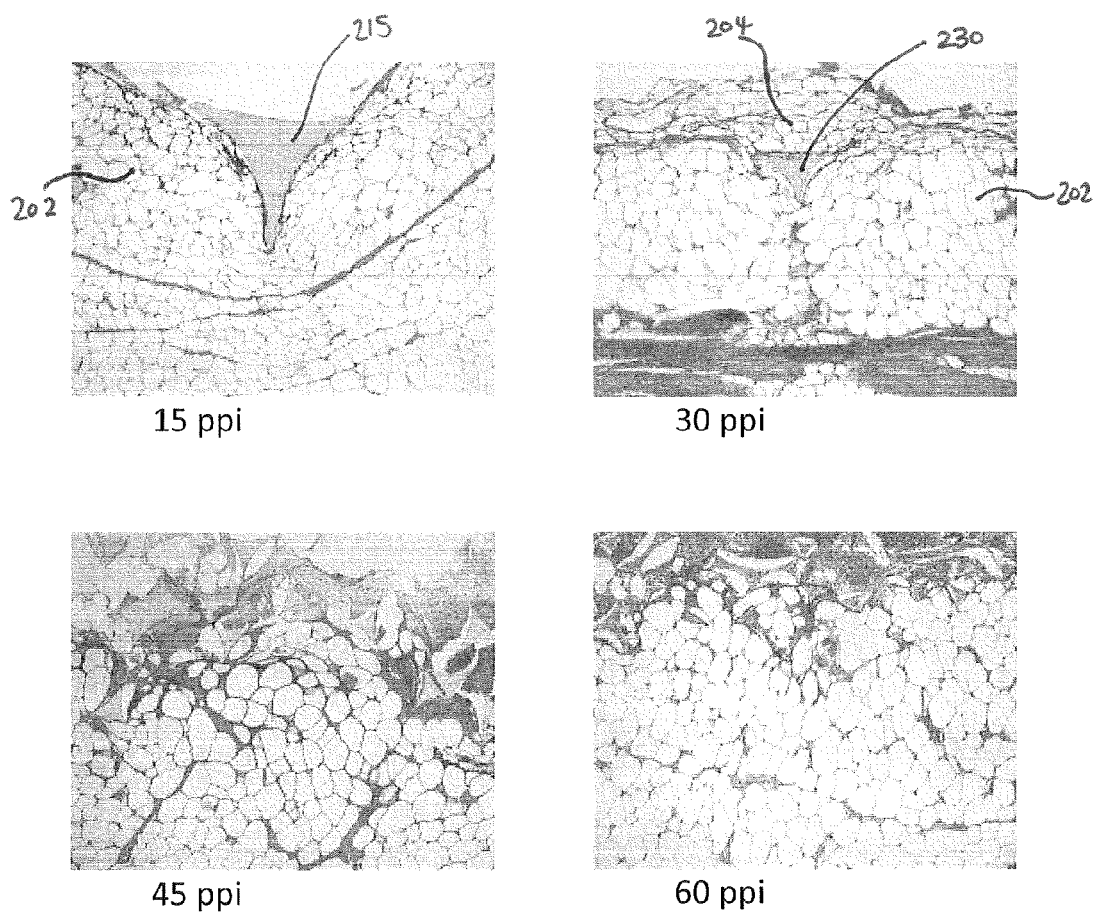
FIG. 10 shows images of foams contacting a wound bed after NPWT.

The above-mentioned histological review of the wound sites and foams were also used to inspect whether any in-growth of tissue into the foam was present after the 72 hour NPWT session. As shown in FIG. 10, the strut 215 of the 15 ppi foam is deeply embedded into the wound bed 202, yet there is no tissue formation growing over the strut. In contrast, the strut 230 of the 30 ppi foam has a visibly significant amount of tissue growth located over the strut. As such, it is likely that the foams with visible tissue growth over the struts would damage that overlying tissue upon removal of the foam from the wound site.

Figure 11:
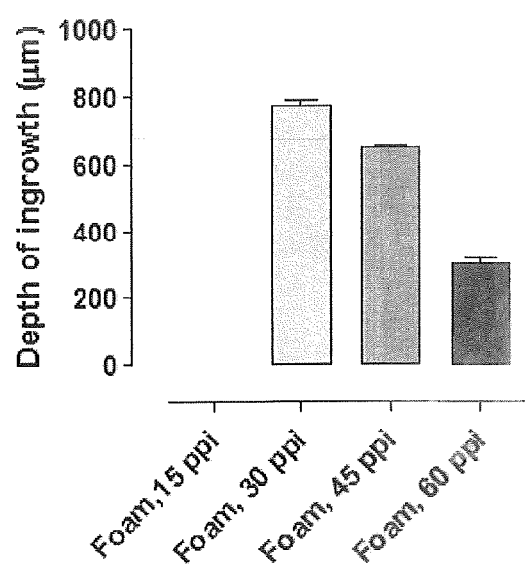
FIG. 11 is a graph of tissue in-growth depth for different foams after NPWT.

In addition to the visual inspection, the depth of the tissue growth into the foam was also measured for each foam sample histologically. As shown in FIG. 11, it can be seen that the 15 ppi foam had a growth depth of 0 µm (i.e. no tissue grew beyond the foam struts), whereas the other samples have significantly larger amount of growth, of at least 300 µm or more above the foam struts. Preferably the growth depth is zero to avoid the drawbacks mentioned above such as patient pain on removal of the wound filler. However, a growth depth of 100 µm or 50 µm or less is better than the larger growth depths exhibited by the foams of 30 ppi and above.

Figure 12:
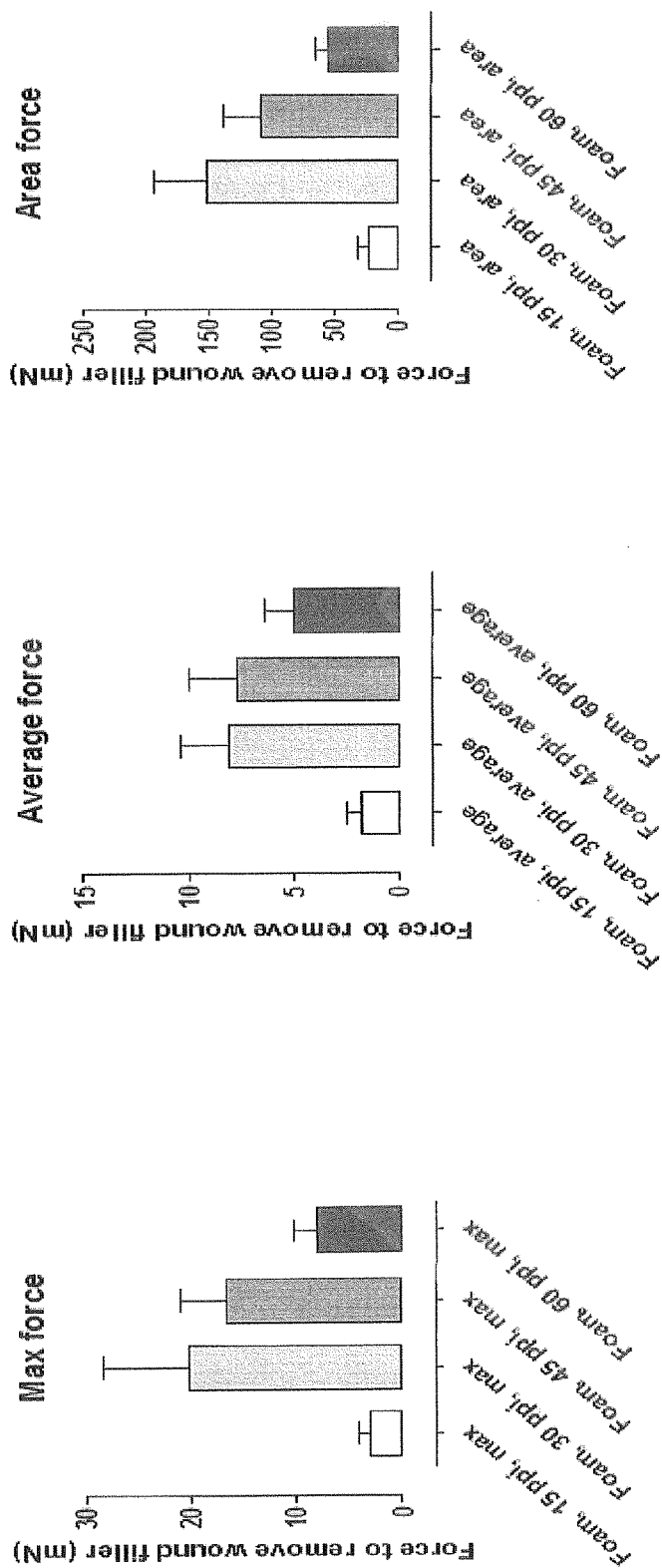
FIG. 12 show graphs of various force measurements to remove different foams after NPWT.

Furthermore, the inventors went on to measure the force required to remove foam pieces of various pore counts from a wound after the above-described 72 hour NPWT session. This was achieved by attaching a rig to the foam piece, the rig being tied to a force measuring device (a Newtonmeter). The rig included four pairs of forceps attached at equal spacing to the foam piece, and each set of forceps being attached by wire to the hook of the Newtonmeter. The Newtonmeter was suspended above the wound site, and connected via a cord to a computer for recording the force over time. The Newtonmeter was pulled in a direction directly away from the wound site at a constant speed of 4 mm/s and the force required to remove the foam from the wound site was recorded. Maximum force, average force and area force were recorded (in mN). For each measurement, the computer recorded force readings over the time period the sample was being pulled away from the wound. Maximum force was the maximum force needed over that pull-out period for each sample. Average force was the average (mean) force of all the readings taken over that pull-out period for each sample. The results are shown graphically in FIG. 12, and below in Table 2. It can be seen that the 15 ppi foam showed a significantly lower maximum force required, average force required, and area force.

It is believed that the distinctly lower force required to remove the 15 ppi foam from the wound site supports the fact that zero or minimal in-growth occurred in the 15 ppi foam.

Aptly, the average pull-out force under the above-mentioned conditions is between about 0.1 and about 5 mN. An average pull-out force of between about 0.1 and about 3 mN is more apt, and between 0.1 and 2 mN is even more apt.

As such, the average pull-out force per unit area is aptly less than 0.177 $mN/cm^2$, or more aptly less than 0.106 $mN/cm$ or more aptly less than 0.071 $mN/cm^2$.

TABLE 2

| Parameter (mN) | 15 ppi | 30 ppi | 45 ppi | 60 ppi |
|---|---|---|---|---|
| Maximum pull-out force - raw data from 8 samples | 9, 0.35, 2.7, 1.2, 4, 1.3, 3.9, 1.3 | 13, 13, 6, 8, 0.6, 30, 73, 17 | 41, 16, 9, 37, 7, 12, 22, 24 | 7, 6, 4, 2, 4, 15, 6, 20 |
| Maximum pull-out force - mean of 8 samples | 2.96875 | 20.075 | 21 | 8 |
| Maximum pull-out force - Standard deviation (mean of standard error) | 0.98139 | 8.16385 | 4.45614 | 2.19578 |
| Average pull-out force - raw data from 8 samples | 6, 0.2, 1.5, 0.7, 2.1, 0.7, 2.3, 0.8 | 8, 7, 2, 7, 0.4, 14, 21, 5 | 10, 8, 6, 19, 3, 8, 11, 15 | 5, 4, 2, 1, 2, 10, 4, 12 |
| Average pull-out force - mean of 8 samples | 1.7875 | 8.05 | 10 | 5 |
| Average pull-out force - | 0.65532 | 2.35182 | 1.79284 | 1.40153 |

TABLE 2-continued

| Parameter (mN) | 15 ppi | 30 ppi | 45 ppi | 60 ppi |
|---|---|---|---|---|
| Standard deviation (mean of standard error) | | | | |
| Area under force-time curve - raw data from 8 samples | 75, 0.46, 15.1, 4.8, 37, 6.4, 38, 7 | 95, 97, 98, 124, 0.93, 254, 383, 154 | 201, 91, 112, 224, 98, 102, 132, 145 | 71, 61, 46, 14, 37, 92, 15, 96 |
| Area under force-time curve - mean of 8 samples | 22.97 | 150.74125 | 138.125 | 54 |
| Area under force-time curve - Standard deviation (mean of standard error) | 9.02205 | 41.52290 | 17.54121 | 11.19630 |

Example 3

The inventors tested parameters of a number of foam pieces having different pore counts including 10 ppi, 15 ppi, 20 ppi and 30 ppi. The results are shown in Table 3. The results shown in Table 3 relate to uncompressed (at rest) foam samples, unless labelled as 'under compression'. For the 'under compression' data, samples of 40 mm×18 mm×30 mm (thickness of 30 mm) were compressed by sandwiching between two plastic slides and taping together, such that the sample had a thickness of 6 mm.

TABLE 3

| Parameter | 10 ppi | 15 ppi | 20 ppi | 30 ppi |
|---|---|---|---|---|
| Nominal pore count (ppi) | 10 | 15 | 20 | 30 |
| Pore size as calculated from ppi (mm) | 2.54 | 1.69 | 1.27 | 0.85 |
| Pore size range - under compression, as measured by micro-CT (mm) | 0.25-1.62 | 0.25-1.42 | 0.22-1.32 | 0.15-0.89 |
| Most frequent pore size - under compression, as measured by micro-CT (mm) | 1.25 | 0.87 | 0.66 | 0.50 |
| Pore size range - not compressed, as measured by micro-CT (mm) | 3.13-5.49 | 2.72-4.16 | 2.31-3.75 | 1.08-2.21 |
| Most frequent pore size - not compressed, as measured by micro-CT (mm) | 4.70 | 3.40 | 3.30 | 1.85 |
| Strut width as measured by micro-CT (mm) | 0.007-0.631 | 0.007-0.617 | 0.007-0.340 | 0.007-0.256 |

TABLE 3-continued

| Parameter | 10 ppi | 15 ppi | 20 ppi | 30 ppi |
|---|---|---|---|---|
| Strut width as measured by SEM (mm) | 0.238-0.951 | 0.098-0.645 | 0.193-0.494 | 0.121-0.659 |
| Strut width as measured by optical microscopy (mm) | 0.354-0.697 | 0.253-0.489 | 0.279-0.404 | 0.173-0.349 |
| Surface area as measured by micro-CT (mm$^2$ in a 126 mm$^3$ volume) | 54 | 92 | 89 | 203 |
| Initial Modulus (Strain 1-4%) (kPa) | 80.8-88.0 | 92.8-96.7 | 105.3-107.8 | 124.4-142.2 |
| Void Volume As measured by micro-CT (%) | 97.1 | 97.2 | 97.5 | 96.5 |
| Density (g/cm$^3$) | 0.033-0.036 | 0.031-0.033 | 0.033 | 0.038-0.039 |
| Compressive Strain at −120 mm Hg % | 74.9-75.8 | 77.8-79.4 | 76.3-77.3 | 73.9-75.1 |

Example 4

The inventors tested the surface area of a number of foams of different ppi in an uncompressed and compressed state. The results are shown below in Table 4. The surface area was measured by micro-CT using the techniques described below under "Measurement techniques". For the 'compressed' data, samples of 40 mm×18 mm×30 mm (thickness of 30 mm) were compressed by sandwiching between two plastic slides and taping together, such that the sample had a thickness of 6 mm.

TABLE 4

| Foam ppi | Surface area Uncompressed (mm$^2$ in a 126 mm$^3$ volume) | Surface area Compressed (mm$^2$ in a 126 mm$^3$ volume) |
|---|---|---|
| 10 | 54 | 409 |
| 15 | 92 | 416 |
| 20 | 89 | 473 |
| 30 | 203 | 862 |
| 45 | 202 | 947 |
| 60 | 336 | 1402 |

Example 5

The inventors investigated the distribution of pore size and strut thickness of foam samples having different ppi. The foam samples were investigated using micro-CT analysis, as described below under 'Measurement techniques'.

Figure 13A:
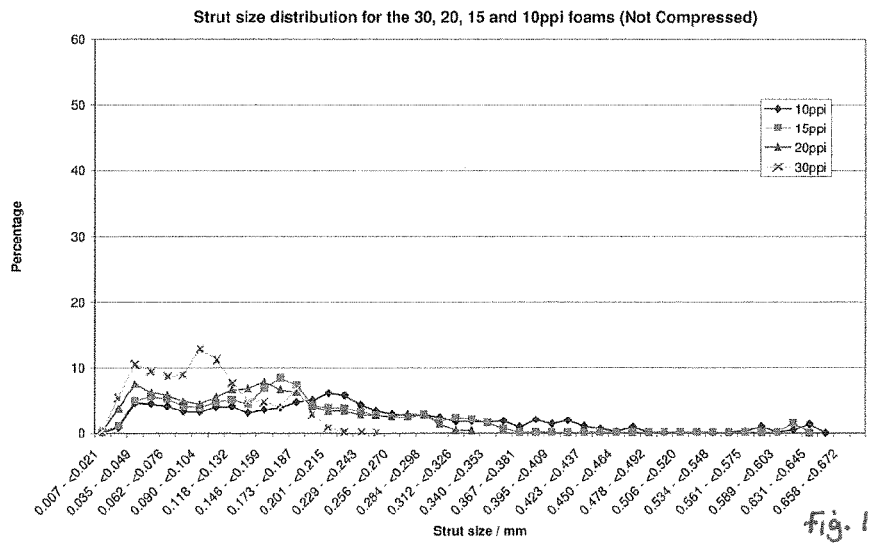
FIG. 13a illustrates strut size measurements for various foams in an uncompressed state.
Figure 13B:
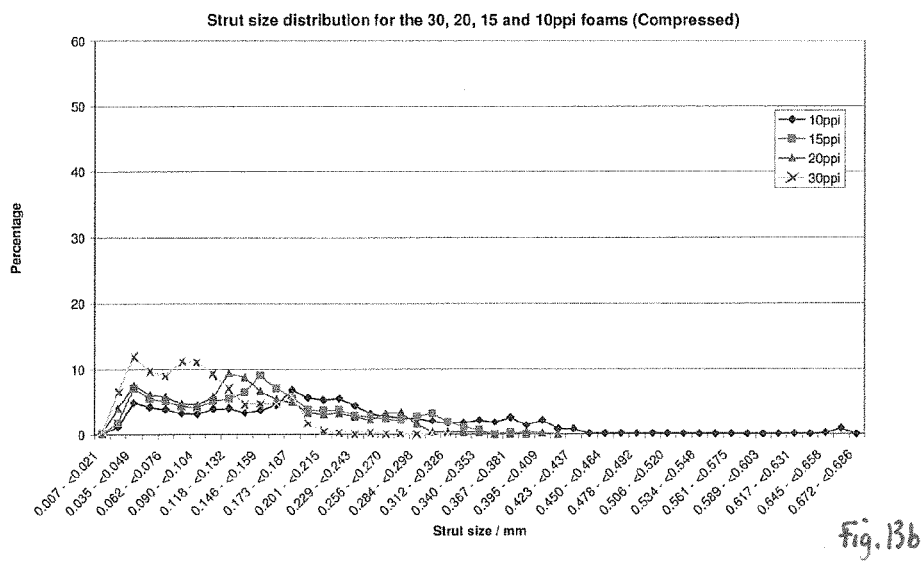
FIG. 13b illustrates strut size measurements for various foams in a compressed state.
Figure 13C:
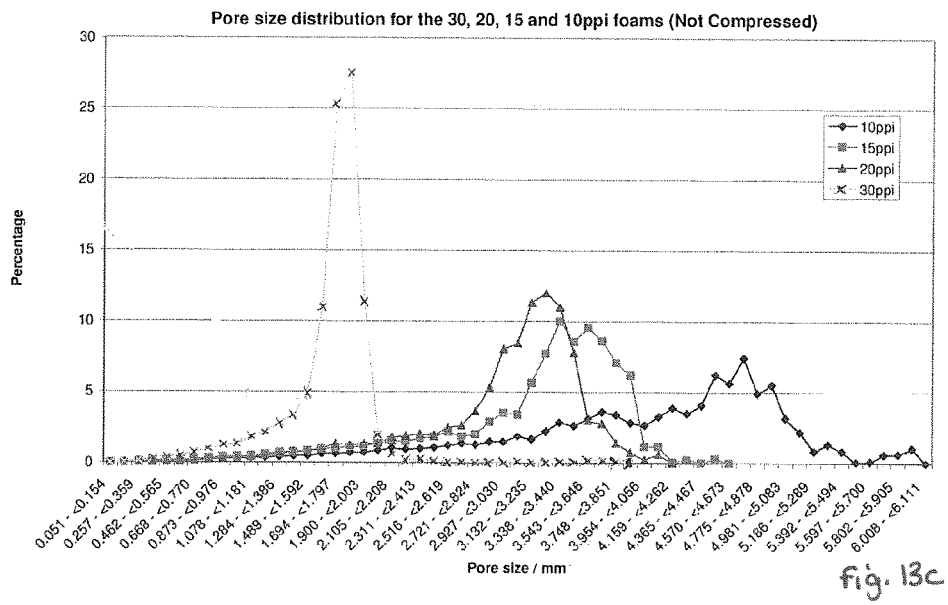
FIG. 13c illustrates pore size measurements for various foams in an uncompressed state.
Figure 13D:
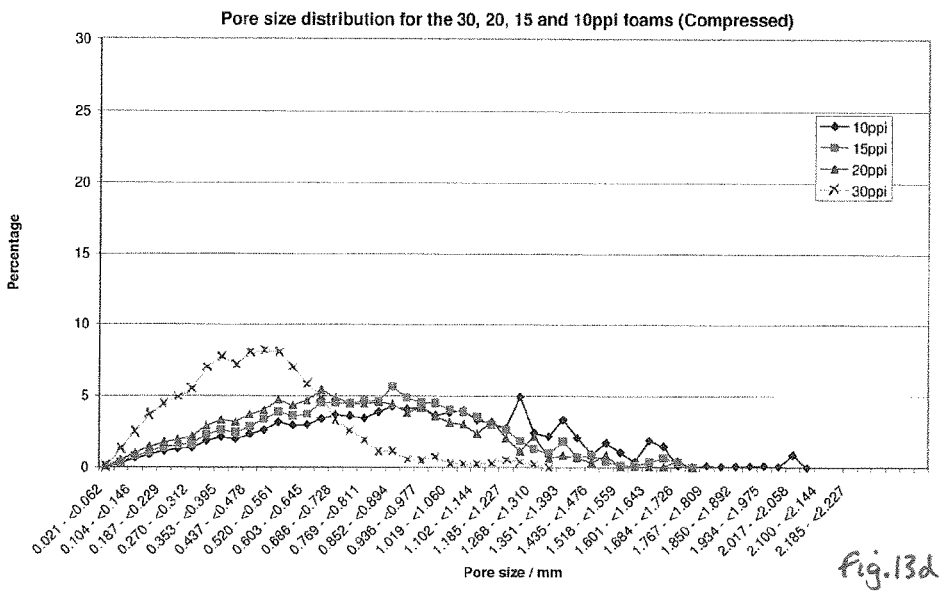
FIG. 13d illustrates pore size measurements for various foams in a compressed state.

Foam samples of various different ppi were investigated. Results of notable interest are shown in FIGS. 13a to 13d. Specifically, FIG. 13a illustrates a graph showing the percentage of total struts at each strut size present, for foams of different ppi under no compression. A graph showing the percentage of total struts at each strut size present, for foams of different ppi under compression is shown in FIG. 13b. A graph showing the percentage of total pores at each pore size present, for foams of different ppi under no compression is shown in FIG. 13c. A graph showing the percentage of total pores at each pore size present, for foams of different ppi under compression is shown in FIG. 13d.

Measurement Techniques

Micro-CT (Micro Computed Tomography)

The sample preparation for the Micro-CT analysis involved fixing a section of approximately 25 mm by 25 mm by 70 mm in height of the NWPT foam directly onto a brass pin sample holder (noting that the actual imaged area equated to approximately 14 mm in height).

The Micro-CT images were acquired on a Skyscan 1172 Micro-CT using a micro focused X-ray source with a voltage of 60 kV and a current of 167 µA. X-ray shadow images were acquired with a 0.2 deg step size over a 180 deg acquisition angle, with a pixel resolution of 5 µm×5 µm. Foams were also imaged using a 0.4 deg step size, with a pixel resolution of 17 µm×17 µm and using a double scan that resulted in an imaged height of ~28 mm. This was to encompass more of the foam sample, especially the larger pore sizes for these foams. The X-ray shadow images were reconstructed to 3D cross-sections using a reconstruction program (N-Recon) supplied by Skyscan.

For the Micro-CT calculations a Volume Of Interest (VOI) was selected from the acquired images that encompassed a proportion of the struts and pores. A VOI was selected in order to reduce the computational processing time to around 3 hours per sample and varied depending on the pore size of the foam.

The following parameters were calculated:
Strut size
Strut surface area (normalised to the volume of interest [VOI] for the 80 ppi foam (126 mm$^3$) to allow a comparison between the foams to be carried out)
Pore size
% void volume Strut surface area was calculated from the data acquired during the CT scan. A volume of interest for each foam sample is found, and then normalised to that of an 80 ppi sample to allow comparisons to be made. Specifically, in a given volume of 126 mm$^3$ foam, the surface area of all external surfaces of the struts present was found.

Strut size was calculated by a sphere fitting model and involved the acquisition of multiple measurements from each strut over a number of struts. A number of spheres were fitted to each strut as closely as possible to match the strut dimensions, and the diameter of each sphere was measured by SEM. The strut width ranges noted above in Table 2 are the distribution of all diameters for all struts viewed.

Pore size calculation was based upon a computational procedure in which a sphere is fitted into the pore space and the diameter of the sphere is measured and taken as the pore size.

Scanning Electron Microscopy

Images were collected using a FEI Inspect S SEM operating at 5 kV accelerating voltage, spot size 2.5. Images were collected at 80× magnification. A selection of strut widths of compressed foams was measured using the instrument software.

Optical Microscopy

Light microscope images were collected using a Zeiss Discovery V12 stereomicroscope with Axiovision software. A selection of strut widths of compressed foams was measured using the instrument software.

Initial Modulus (Young's Modulus)

To prepare the foams for compression testing, circular sections were cut out using a cutter (54 mm Æ) and a hydraulic press. The vertical height of each foam section was then allowed to recover (~6 hrs) before being measured with a thickness gauge. The measured foams were then tested in uniaxial compression on an Instron 5569. The utilised test parameters are shown in Table 5.

TABLE 5

| Test parameters | |
|---|---|
| Parameter | Utilised value |
| Preload | 0.01N applied at 1 mm min$^{-1}$ |
| Compression rate | 20 mm min$^{-1}$ |
| Test stop value | 75% strain |
| Top loading platen diameter | 50 mm |
| Bottom loading platen diameter | 150 mm |
| Recovery time between repeat tests. | overnight |
| Data capture rate | 10 Hz |
| Load cell | 100N static load cell |

The Young's modulus was calculated between 1 and 4% strain using an automatic algorithm in the Instron Bluehill (Version 2.6) control software.

Density

The dimensions of a foam block (approximately 70 mm$^2$) were measured using a digital caliper and then the volume of the block was calculated. The foam block was then weighed and the density calculated.

Compressive Strain at −120 mmHg

Figure 14:
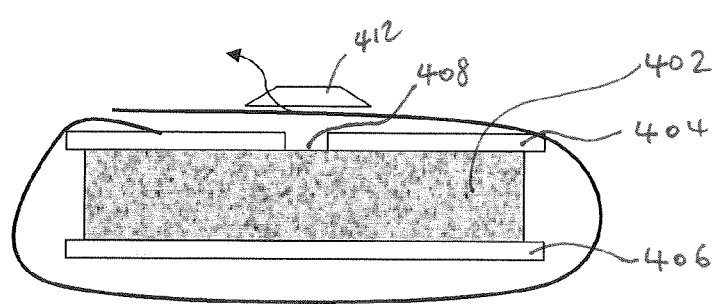
FIG. 14 illustrates apparatus to measure compressive strain.

The basic experimental set-up is shown in FIG. 14. A foam sample 402 is positioned between a set of Perspex sheets 404, 406, the top sheet having an aperture 408. The method includes the following steps.

1. Place the Perspex plates and foam sample on to a piece of plastic wrap (cling film) 410 (large enough to enclose all components) in the order shown in FIG. 14.
2. Fold the plastic wrap around the components to completely seal the system ensuring that one side of the top of the plates is smooth and covered only by one layer of cling film to allow measurement.
3. Measure the thickness of the entire system (A) using a digital caliper.
4. Make a small hole in the film over the aperture in the top plate.
5. Position a vacuum port 412 connected to a pump, such as the Renasys EZ pump available from Smith & Nephew PLC (not shown), over the hole and hold while switching on the pump (set at −120 mmHg or desired level). There will be enough adhesion between the port and film to maintain a seal.
6. Ensure the foam sucks down and wait 60 seconds before measuring the new thickness. This time lapse is required to ensure the foams have compressed as far as possible.
7. Measure the thickness (B) in the same position as the initial measurement.
8. Blank measurements (C) are made using the above method but omitting the foam.
9. Compressive strain is determined by the following calculation:

Foam thicknesses compressed and uncompressed are calculated by subtracting the blank values from those measured with the foam in place:

Uncompressed foam thickness $D=A-C$

Compressed foam thickness $E=B-C$

% Compressive strain=$(D-E)*100/D$

It is noted that in the present example, pore size was calculated by micro-CT measurements. Of course pore size could also be calculated by using a number of reference materials and a pressure drop, for example.

With the above-described embodiments, a foam for wound filling or wound contacting use is easy to use, promotes granulation tissue growth, and prevents or reduces tissue in-growth. Further benefits include reduced risk of infection due to dressing changes, reduced patient discomfort, reduced clinician time in applying or removing the wound care arrangement, and possibility of increased contact time of the filler with a wound.

Various modifications to the detailed designs as described above are possible. For example, although a foam material has been used in the above described embodiments, it would be possible (although not necessarily as advantageous) to use other substrates to contact the wound, such as nets or polymer slabs containing perforations. For example, the net could be scrunched to pack a wound so that the wound bed is in contact with the pores of the net. The net, polymer slab and/or foam could be used in combination as a wound contacting member. For example, a styrene/butadiene copolymer net mesh with dimensions 1.5×2 mm and a strut width of 0.25 mm and thickness of 0.4 mm (such as is available from Conwed Plastics, Minneapolis, USA under product code XO 2550-002 SBD) could be used. Alternatively a thermoplastic polyurethane with pore size 0.6×1.0 mm and strut width of 0.4 mm and thickness 0.5 mm (also available from Conwed under product code TP2000-001TPU) could be used.

As described above, it will be appreciated that the materials may be used in conjunction with NPWT, as a wound filler, for example, or as a stand-alone wound contacting member for wound dressing purposes. The foam may only partially fill a wound, may be used in conjunction with other materials, or equally may be used as a wound contact layer of a dressing suitable for shallower wounds, for example.

Other embodiments can be seen in the following paragraphs:

Apparatus for the treatment of wounds in a human or animal subject by negative pressure wound therapy (NPWT), comprising: a wound contacting member for applying to a wound bed; a cover member configured to form a sealed enclosure around the wound contacting member when the wound contacting member is applied to the wound bed, wherein, in use after NPWT has been applied to the sealed enclosure for 3 days, the wound contacting member shows an absence of anchor points. Alternatively, the wound contacting member may show less than 10%, or more preferably 5% coverage of anchor points, wherein the percentage of anchor points is calculated based on the number of struts juxtaposed with the wound bed available to form anchor points on a surface of the wound contacting member. For example, if in a given area there are 100 struts notionally available to the wound bed to form anchor points and 5 struts do form anchor points, then this is 5%.

A method of treating a wound in a human or animal subject, comprising: applying a wound contacting member to contact a wound bed, covering the wound contacting member with a cover member to form a sealed enclosure; and applying NPWT to the sealed enclosure for 3 days, wherein after the step of applying NPWT the wound contacting member shows an absence of anchor points. Alternatively, the wound contacting member may show less than 10%, or more preferably 5% coverage of anchor points.

Apparatus for the treatment of wounds in a human or animal subject by negative pressure wound therapy (NPWT), comprising: a wound contacting member for applying to a wound bed; a cover member configured to form a sealed enclosure around the wound contacting member when the wound contacting member is applied to the wound bed, wherein, in use after 2 or 3 days of NPWT the wound contacting member can be removed from the wound bed by a force of less than 5 mN. Aptly, the wound contacting member can be removed by a force of less than 3 mN, and more aptly 2 mN.

A method of treating a wound in a human or animal subject, comprising: applying a wound contacting member to contact a wound bed, applying NPWT to the wound for 2 or 3 days, wherein after the NPWT the wound contacting member can be removed from the wound bed by a force of less than 5 mN. Aptly, the wound contacting member can be removed by a force of less than 3 mN, and more aptly 2 mN.

A method of treating a wound in a human or animal subject, comprising: applying a wound contacting member to contact a wound bed, wherein the wound contacting member having a network of strut elements separated by pores wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT, and then covering the wound contacting member with a cover member to form a sealed cavity, and applying negative pressure to the cavity, thereby promoting granulation tissue growth at the wound bed, and after a predetermined period of time, removing the wound contacting member from the wound bed, wherein the wound contacting member can be removed from the wound bed by a force of less than 5 mN. Aptly, the wound contacting member can be removed by a force of less than 3 mN, and more aptly 2 mN.

A method of treating a wound in a human or animal subject, comprising: applying a wound contacting member to contact a wound bed, the wound contacting member having a network of struts separated by pores, wherein at least 95% of the struts have a thickness of between 0.007 and 0.5 mm, and the wound contacting member has at least one strut having a thickness of 0.23 mm or more, as measured by micro-CT, and the wound contacting member having a compressive strain at −120 mmHg of between about 50 and about 90%, and then covering the wound contacting member with a cover member to form a sealed cavity, and applying negative pressure to the cavity, thereby promoting granulation tissue growth at the wound bed, and after a predetermined period of time, removing the wound contacting member from the wound bed, wherein the wound contacting member can be removed from the wound bed by a force of less than 5 mN. Aptly, the wound contacting member can be removed by a force of less than 3 mN, and more aptly 2 mN.

A method of treating a wound in a human or animal subject, comprising: applying a-wound contacting member to contact a wound bed, the wound contacting member having a network of struts separated by pores, wherein at least 95% of the struts have a thickness of between 0.007 and 0.5 mm, and the wound contacting member has at least one strut having a thickness of 0.23 mm or more, and the struts have a total surface area of between 30 and 150 mm$^2$ in a 126 mm³ volume, as measured by micro-CT, and then covering the wound contacting member with a cover member to form a sealed cavity, and applying negative pressure to the cavity, thereby promoting granulation tissue growth at the wound bed, and after a predetermined period of time, removing the wound contacting member from the wound bed, wherein the wound contacting member can be removed from the wound bed by a force of less than 5 mN. Aptly, the wound contacting member can be removed by a force of less than 3 mN, and more aptly 2 mN.

A foam having pores having at least 90% of the pores have a diameter of between 2.3 and 5.5 mm, and at least 90% of the pores have a diameter of 2.5 mm or greater, as measured by micro-CT, and a pull-out force of less than 5 mN when applied to a wound bed of a human or animal subject and tested under 72 hours NPWT. Aptly, the foam can be removed by a force of less than 3 mN, and more aptly 2 mN.

A foam having struts wherein at least 95% of the struts have a thickness of between 0.007 and 0.5 mm, and the foam has at least one strut having a thickness of 0.23 mm or more, as measured by micro-CT, and a pull-out force of less than 5 mN when applied to a wound bed of a human or animal subject and tested under 72 hours NPWT. Aptly, the foam can be removed by a force of less than 3 mN, and more aptly 2 mN.

In a method of NPWT for the promotion of wound healing, the improvement comprising using a foam comprising a network of strut elements separated by pores, at least 90% of the pores having a diameter of between 2.3 and 5.5 mm, and at least 90% of the pores have a diameter of 2.5 mm or greater, as measured by micro-CT.

In a method of NPWT for the promotion of wound healing, the improvement comprising using a foam comprising a network of strut elements separated by pores, at least 95% of the strut elements have a thickness of between 0.007 and 0.5 mm, and the foam has at least one strut element having a thickness of 0.23 mm or more, as measured by micro-CT, and the foam having a compressive strain at −120 mmHg of between about 50 and about 90%.

In a method of NPWT for the promotion of wound healing, the improvement comprising using a foam comprising a network of strut elements separated by pores, wherein at least 95% of the strut elements have a thickness of between 0.007 and 0.5 mm, and the foam comprises one or more strut element having a thickness of 0.23 mm or more, and the strut elements have a total surface area of between 30 and 150 mm² in a 126 mm³ volume, as measured by micro-CT.

A method of promoting healing of a wound in a human or animal patient, comprising applying to a surface of the wound a wound filler having pores, at least 90% of the pores have a diameter of between 2.3 and 5.5 mm, and at least 90% of the pores having a diameter of 2.5 mm or greater, and at least 95% of struts separating the pores having a thickness of between 0.007 and 0.5 mm, as measured by micro-CT; and subjecting the wound filler to a negative pressure.

A method of promoting healing of a wound in a human or animal patient, comprising applying to a surface of the wound a wound filler having struts, at least 95% of the struts have a thickness of between 0.007 and 0.5 mm, and the filler having at least one strut having a thickness of 0.23 mm or more, as measured by micro-CT, and the filler having a compressive strain at −120 mmHg of between about 50 and about 90%; and subjecting the wound filler to a negative pressure.

A method of promoting healing of a wound in a human or animal patient, comprising applying to a surface of the wound a wound filler having struts, and at least 95% of the struts having a thickness of between 0.007 and 0.5 mm, and the filler comprising one or more strut having a thickness of 0.23 mm or more, and the struts having a total surface area of between 30 and 150 mm² in a 126 mm³ volume, as measured by micro-CT; and subjecting the wound filler to a negative pressure.

A method of treating a wound in a human or animal subject, comprising: applying a wound contacting material to a wound bed, applying negative pressure to the wound filler to form an imprint in the wound bed of between 900 and 1200 μm. Aptly negative pressure is applied to form an imprint of between 900 and 1000 μm.

A wound contacting member for negative pressure wound therapy (NPWT), comprising a network of strut elements separated by pores, wherein the strut elements are spaced apart by a distance sufficient to promote granulation tissue growth at the wound bed yet substantially prevent tissue in-growth.

A method of testing the suitability of a wound contacting member, comprising: applying a wound contacting member to a porcine wound; for a predetermined period of time applying NPWT; and determining the suitability of the wound contacting member by removing the wound contacting member with a force of less than 5 mN. Aptly, the wound contacting member can be removed by a force of less than 3 mN, and more aptly 2 mN.

A wound dressing comprising a wound contacting member, wherein when the wound contacting member is applied to a porcine wound; and for a predetermined period of time NPWT is applied, the wound contacting member can be removed from the wound with a force of less than 5 mN. Aptly, the wound contacting member can be removed by a force of less than 3 mN, and more aptly 2 mN.

A wound contacting member for use in negative pressure wound therapy (NPWT) comprising a network of strut elements separated by pores, the pores and strut elements being configured such that when, in use, the wound contacting member is contacted with a wound surface of a mammalian subject for a period of 72 hours during which NPWT is applied, of the first struts encountered when moving along any lines extending orthogonally away from the wound bed, at least 90% have a surface distal from the wound bed which is not in contact with tissue. More preferably 95% or 99% or 100% of the first struts have a surface distal from the wound bed which is not in contact with tissue.

Yet other embodiments can be seen in the following paragraphs:

1. A method for treating a wound, comprising:
   positioning a wound contacting member into contact with the wound, the wound contacting member comprising a network of struts separated by pores and having a pore size of between 5 and 25 ppi;
   positioning a cover over the wound contacting member to form a sealed environment over the wound;
   providing negative pressure from a vacuum source in fluid communication with the sealed environment to transmit negative pressure through the wound contacting member to the wound;
   applying negative pressure to the wound for at least 72 hours in the range of −40 mmHg to −200 mmHg, the negative pressure and the wound contacting member promoting the growth of granulation tissue at the wound, wherein the negative pressure causes the wound contacting member to compress to decrease the void volume and increase the strut volume; and removing the cover and the wound contacting member from the wound, wherein the force required to remove the wound contacting member from the wound is less than 5 mN.

2. The method of paragraph 1, wherein at least 90% of the pores have a diameter of between 2.3 and 5.5 mm as measured by micro-computed tomography.

3. The method of paragraph 1 or 2, wherein at least 95% of the struts have a thickness between 0.007 and 0.5 mm as measured by micro-computed tomography.

4. The method of any of paragraphs 1-3, wherein the application of negative pressure to the wound causes the wound contacting member to indent into tissue of the wound by about 950 to about 1000 μm.

5. The method of any of paragraphs 1-4, wherein the wound contacting member has a compressive strain at −120 mmHg of between about 50% and about 90%.

6. The method of any of paragraphs 1-5, wherein the wound contacting member comprises foam.

7. The method of any of paragraphs 1-6, wherein prior to the step of applying negative pressure, the wound contacting member has a pore volume of about 90 to about 98% of the total volume, and after the step of applying negative pressure for at least 72 hours, the wound contacting member has a pore volume of about 70 to about 90% of the total volume.

8. The method of any of paragraphs 1-7, wherein after the step of applying negative pressure for at least 72 hours, the wound contacting member shows an absence of anchor points.

9. A method of measuring in-growth of tissue into a wound contacting member under negative pressure, comprising:
   positioning a wound contacting member into contact with the tissue, the wound contacting member comprising a network of struts separated by pores;
   positioning a cover over the wound contacting member to form a sealed environment;
   applying negative pressure from a vacuum source in fluid communication with the sealed environment to transmit negative pressure through the wound contacting member to the tissue; and
   measuring the in-growth of tissue into the wound contacting member, wherein said measurement is performed by one or both of:
      (i) measuring the number of points at which tissue is anchored to the wound contacting member; and
      (ii) measuring the amount of force needed to remove the wound contacting member from the tissue.

10. The method of paragraph 9, wherein the wound contacting member comprises foam.

11. The method of paragraph 9 or 10, wherein the tissue is wound tissue of a patient.

12. The method of any of paragraphs 9-11, wherein the tissue is animal tissue.

13. The method of any of paragraphs 9-12, wherein the tissue is experimental tissue.

14. The method of any of paragraphs 9-13, wherein the negative pressure is applied to the wound for at (east 72 hours in the range of −40 mmHg to −200 mmHg.

15. A wound contacting member for negative pressure wound therapy (NPWT), comprising a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

16. The wound contacting member of paragraph 15, wherein at least 95% of the pores have a diameter between 2.3 and 5.5 mm.

17. The wound contacting member of paragraph 16, wherein at least 95% of the pores have a diameter of 2.5 mm or greater.

18. The wound contacting member of paragraphs 15-17, wherein the most frequent pore size is between 3 and 5 mm.

19. The wound contacting member of paragraph 18, wherein the most frequent pore size is between 3.3 and 4.7 mm.

20. The wound contacting member of paragraphs 15-19, wherein at least 10% of the strut elements have a thickness of 0.23 mm or more.

21. The wound contacting member of paragraphs 15-20, wherein the wound contacting member has a compressive strain at −120 mmHg of between 50 and 90%.

22. The wound contacting member of paragraph 21, wherein the wound contacting member has a compressive strain at −120 mmHg of between 50 and 80%.

23. The wound contacting member of paragraph 22, wherein the wound contacting member has a compressive strain at −120 mmHg of between 55 and 75%.

24. The wound contacting member of paragraphs 15-23, wherein the wound contacting member has a surface area of between 30 and 150 mm$^2$ in a 126 mm$^3$ volume, as measured by micro-CT.

25. The wound contacting member of paragraph 24, wherein the wound contacting member has a surface area of between 45 and 100 mm$^2$ in a 126 mm$^3$ volume, as measured by micro-CT.

26. The wound contacting member of paragraph 25, wherein the wound contacting member has a surface area of between 50 and 95 mm$^2$ in a 126 mm$^3$ volume, as measured by micro-CT.

27. The wound contacting member of paragraphs 15-26, wherein the wound contacting member promotes granulation tissue growth at a wound bed simultaneously with the prevention or reduction of tissue in-growth into the wound contacting member.

28. The wound contacting member of paragraphs 15-27, wherein the wound contacting member is a foam.

29. The wound contacting member of paragraph 28, wherein the wound contacting member is a reticulated foam.

30. The wound contacting member of paragraph 28 or 29, wherein the foam is polyurethane.

31. The wound contacting member of paragraph 30, wherein the foam is polyether polyurethane.

32. The wound contacting member of paragraphs 15-32, wherein the density of the wound contacting member is between 0.03 and 0.04 g·cm$^{-3}$.

33. Apparatus for the treatment of wounds in a human or animal subject by negative pressure wound therapy (NPWT), comprising:
   a wound contacting member for applying to a wound bed;
   a cover member configured to form a sealed enclosure around the wound contacting member when the wound contacting member is applied to the wound bed,
   wherein the wound contacting member comprises a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

34. The apparatus of paragraph 33, further comprising a connection device for placing the enclosure in fluid communication with a vacuum source.

35. A kit for use in negative pressure wound therapy (NPWT), comprising
   a wound contacting member for applying to a wound bed;
   a cover member configured to form a sealed enclosure around the wound contacting member when the wound contacting member is applied to the wound bed,
   wherein the wound contacting member comprises a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

36. A method of treating a wound in a human or animal subject, comprising:
   applying a wound contacting member to a wound bed, wherein
   the wound contacting member comprises a network of strut elements separated by pores, wherein at least 90% of the pores have a diameter of between 2.3 and 5.5 mm, and at least 90% of the pores have a diameter of 2.5 mm or greater, and at least 95% of the strut elements have a thickness of between 0.007 and 0.5 mm, and the wound contacting member includes one or more strut element having a thickness of 0.23 mm or more, as measured by micro-CT.

37. The method of paragraph 36, further comprising the step of applying a cover member over the wound contacting member to form a sealed enclosure.

38. The method of paragraphs 36 or 37, further comprising the step of applying negative pressure wound therapy (NPWT) to the wound bed.

39. The method of any of paragraphs 36 to 38, further comprising the step of promoting granulation tissue growth at the wound bed simultaneously with preventing or reducing tissue in-growth into the wound contacting member.

40. The wound contacting member for negative pressure wound therapy (NPWT), comprising a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

41. The wound contacting member of paragraph 40, wherein the wound contacting member has a compressive strain at −120 mmHg of between 50 and 80%.

42. The wound contacting member of paragraph 41, wherein the wound contacting member has a compressive strain at −120 mmHg of between 55 and 75%.

43. The wound contacting member of paragraphs 40-42, wherein at least 90% of the pores have a diameter between 2.3 and 5.5 mm.

44. The wound contacting member of paragraph 43, wherein at least 90% of the pores have a diameter of 2.5 mm or greater.

45. The wound contacting member of paragraphs 43-44, wherein at least 95% of the pores have a diameter between 2.3 and 5.5 mm.

46. The wound contacting member of paragraphs 40-45, wherein the most frequent pore size is between 3 and 5 mm.

47. The wound contacting member of paragraph 46, wherein the most frequent pore size is between 3.3 and 4.7 mm.

48. The wound contacting member of paragraphs 40-47, wherein at least 10% of the strut elements have a thickness of 0.23 mm or more.

49. The wound contacting member of paragraph 40-48, wherein the wound contacting member has a surface area of between 30 and 150 $mm^2$ in a 126 $mm^3$ volume, as measured by micro-CT.

50. The wound contacting member of paragraph 49, wherein the wound contacting member has a surface area of between 45 and 100 $mm^2$ in a 126 $mm^3$ volume, as measured by micro-CT.

51. The wound contacting member of paragraph 50, wherein the wound contacting member has a surface area of between 50 and 95 $mm^2$ in a 126 $mm^3$ volume, as measured by micro-CT.

52. The wound contacting member of paragraphs 40-51, wherein the wound contacting member promotes granulation tissue growth at a wound bed simultaneously with the prevention or reduction of tissue in-growth into the wound contacting member.

53. The wound contacting member of paragraphs 40-52, wherein the wound contacting member is a foam.

54. The wound contacting member of paragraph 53, wherein the wound contacting member is a reticulated foam.

55. The wound contacting member of paragraphs 53 or 54, wherein the foam is polyurethane.

56. The wound contacting member of paragraph 55, wherein the foam is polyether polyurethane.

57. The wound contacting member of paragraph 40-56, wherein the density of the wound contacting member is between 0.03 and 0.04 g·cm−3.

58. Apparatus for the treatment of wounds in a human or animal subject by negative pressure wound therapy (NPWT), comprising:
   a wound contacting member for applying to a wound bed;
   a cover member configured to form a sealed enclosure around the wound contacting member when the wound contacting member is applied to the wound bed,
   wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

59. Apparatus of paragraph 19, further comprising a connection device for placing the enclosure in fluid communication with a vacuum source.

60. A kit for use in negative pressure wound therapy (NPWT), comprising
   a wound contacting member for applying to a wound bed;
   a cover member configured to form a sealed enclosure around the wound contacting member when the wound contacting member is applied to the wound bed,
   wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, as measured by micro- CT, and the wound contacting member has a compressive strain at −120 mmHg of between about 50 and about 90%.

61. A method of treating a wound in a human or animal subject, comprising:
applying a wound contacting member to a wound bed, wherein
the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, as measured by micro-CT, and the wound contacting member has a compressive strain at −120 mmHg of between about 50 and about 90%.

62. The method of paragraph 61, further comprising the step of applying a cover member over the wound contacting member to form a sealed enclosure.

63. The method of paragraphs 61 or 62, further comprising the step of applying negative pressure wound therapy (NPWT) to the wound bed.

64. The method of any of paragraphs 61-63, further comprising the step of promoting granulation tissue growth at the wound bed simultaneously with preventing or reducing tissue in-growth into the wound contacting member.

65. A wound contacting member for negative pressure wound therapy (NPWT), comprising a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

66. The wound contacting member of paragraph 65, wherein the wound contacting member has a surface area of between 45 and 100 mm$^2$ in a 126 mm$^3$ volume.

67. The wound contacting member of paragraph 66, wherein the wound contacting member has a surface area of between 50 and 95 mm$^2$ in a 126 mm$^3$ volume.

68. The wound contacting member of any of paragraphs 65-67, wherein at least 90% of the pores have a diameter of between 2.3 and 5.5 mm.

69. The wound contacting member of paragraph 68, wherein at least 90% of the pores have a diameter of 2.5 mm or greater.

70. The wound contacting member of paragraph 68 or 69, wherein at least 95% of the pores have a diameter of between 2.3 and 5.5 mm.

71. The wound contacting member of any of paragraphs 65-70, wherein the most frequent pore size is between 3 and 5 mm.

72. The wound contacting member of paragraph 71, wherein the most frequent pore size is between 3.3 and 4.7 mm.

73. The wound contacting member of any of paragraphs 65-72, wherein at least 10% of the strut elements have a thickness of 0.23 mm or more.

74. The wound contacting member of any of paragraphs 65-73, wherein the wound contacting member has a compressive strain at −120 mmHg of between 50 and 90%.

75. The wound contacting member of paragraph 74, wherein the wound contacting member has a compressive strain at −120 mmHg of between 50 and 80%.

76. The wound contacting member of paragraph 75, wherein the wound contacting member has a compressive strain at −120 mmHg of between 55 and 75%.

77. The wound contacting member of any of paragraphs 65-76, wherein the wound contacting member promotes granulation tissue growth at a wound bed simultaneously with the prevention or reduction of tissue in-growth into the wound contacting member.

78. The wound contacting member of any of paragraphs 65-77, wherein the wound contacting member is a foam.

79. The wound contacting member of paragraph 78, wherein the wound contacting member is a reticulated foam.

80. The wound contacting member of paragraph 78 or 79, wherein the foam is polyurethane.

81. The wound contacting member of paragraph 80, wherein the foam is polyether polyurethane.

82. The wound contacting member of any of paragraphs 65-81, wherein the density of the wound contacting member is between 0.03 and 0.04 g·cm$^{-3}$.

83. Apparatus for the treatment of wounds in a human or animal subject by negative pressure wound therapy (NPWT), comprising:
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 1.26 mm$^3$ volume, as measured by micro-CT.

84. Apparatus of paragraph 83, further comprising a connection device for placing the enclosure in fluid communication with a vacuum source.

85. A kit for use in negative pressure wound therapy (NPWT), comprising
a wound contacting member for applying to a wound bed;
a cover member configured to form a sealed enclosure around the wound contacting member when the wound contacting member is applied to the wound bed,
wherein the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

86. A method of treating a wound in a human or animal subject, comprising:
applying a wound contacting member to a wound bed, wherein
the wound contacting member comprises a network of strut elements separated by pores, wherein at least 95% of the strut elements have a thickness of between 0.007 and 0.5 mm, and the wound contacting member comprises one or more strut element having a thickness of 0.23 mm or more, and the strut elements have a total surface area of between 30 and 150 mm$^2$ in a 126 mm$^3$ volume, as measured by micro-CT.

87. The method of paragraph 86, further comprising the step of applying a cover member over the wound contacting member to form a sealed enclosure.

88. The method of paragraph 86 or 87, further comprising the step of applying negative pressure wound therapy (NPWT) to the wound bed.

89. The method of any of paragraphs 86 to 88, further comprising the step of promoting granulation tissue growth at the wound bed simultaneously with preventing or reducing tissue in-growth into the wound contacting member.

While the above detailed description has shown, described, and pointed, out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. It will be clear to a person skilled in the art that features described in relation to any of the embodiments described above can be applicable interchangeably between the different embodiments. The embodiments described above are examples to illustrate various features of the invention. All possible combinations and subcombinations are intended to fall within the scope of this disclosure. Many of the embodiments described above include similar components, and as such, these similar components can be interchanged in different embodiments.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A wound contacting member for negative pressure wound therapy (NPWT) selected to reduce pain upon removal from a wound, comprising:
   a foam, the foam comprising:
   a network of foam strut elements separated by pores, at least 95% of the strut elements comprising a thickness of between 0.007 and 0.5 mm;
   wherein one or more foam strut elements comprise a thickness of 0.23 mm or more; and
   wherein at least 90% of the pores comprise a diameter of between 2.3 and 5.5 mm.

2. The wound contacting member of claim 1, wherein the wound contacting member has a pore count of between 5 and 25 ppi.

3. The wound contacting member of claim 1, wherein at least 10% of the strut elements have a thickness of 0.23 mm or more.

4. The wound contacting member of claim 1, wherein the wound contacting member has a compressive strain at −120 mmHg of between 50±5% and 90%±5%.

5. The wound contacting member of claim 1, wherein the strut elements have a total surface area of between 30 and 150 $mm^2$ in a 126 $mm^3$ volume.

6. The wound contacting member of claim 1, wherein the wound contacting member promotes granulation tissue growth at a wound bed simultaneously with the prevention or reduction of tissue in-growth into the wound contacting member.

7. The wound contacting member of claim 1, wherein the wound contacting member has a density between 0.03 and 0.04 $g \cdot cm^{-3}$.

8. An apparatus for treating wounds in a human or animal subject by negative pressure wound therapy (NPWT), comprising:
   the wound contacting member of claim 1; and
   a cover member configured to form a sealed enclosure around the wound contacting member when the wound contacting member is applied to a wound bed.

9. The apparatus of claim 8, further comprising a connection device for placing the enclosure in fluid communication with a vacuum source.

10. A method for treating a wound, comprising applying the wound contacting member of claim 1 to a wound bed.

11. The method of claim 10, further comprising applying a cover over the wound contacting member to form a sealed enclosure.

12. The method of claim 11, further comprising the step of applying negative pressure wound therapy (NPWT) to the wound bed.

13. The method of claim 10, further comprising promoting granulation tissue growth at the wound bed simultaneously with preventing or reducing tissue in-growth into the wound contacting member.

14. The method of claim 12, comprising applying negative pressure to the wound for at least 72 hours in the range of −40 mmHg to −200 mmHg, the negative pressure and the wound contacting member promoting the growth of granulation tissue at the wound, wherein the negative pressure causes the wound contacting member to compress to decrease a void volume and increase a strut volume.

15. The method of claim 12, further comprising removing the cover and the wound contacting member from the wound, wherein a force required to remove the wound contacting member from the wound is less than 5 mN.

16. The method of claim 12, wherein the application of negative pressure to the wound causes the wound contacting member to indent into tissue of the wound by 950±50 μm to 1000±50 μm.

17. The method of claim 12, wherein prior to applying negative pressure, the wound contacting member has a pore volume of 90±5% to 98±5% of the total volume, and after applying negative pressure for at least 72 hours, the wound contacting member has a pore volume of 70±5% to 90±5% of the total volume.

* * * * *

UNITED STATES PATENT AND TRADEMARK OFFICE
CERTIFICATE OF CORRECTION

PATENT NO. : 10,245,185 B2
APPLICATION NO. : 14/124613
DATED : April 2, 2019
INVENTOR(S) : John Kenneth Hicks et al.

It is certified that error appears in the above-identified patent and that said Letters Patent is hereby corrected as shown below:

In the Drawings

On Sheet 7 of 14 (Y-axis), Fig. 7, Line 2, change "inprint" to --imprint--.

On Sheet 7 of 14 (Y-axis), Fig. 8, Line 2, change "inprint" to --imprint--.

In the Specification

In Column 1, Line 61, change "(tissue" to --tissue--.

In Column 3, Line 4, change "WO02009/089016" to --WO2009/089016--.

In Column 10, Line 5, change "wound," to --wound--.

In Column 11, Line 58, change "strut-element" to --strut element--.

In Column 15, Line 45, change "ppi-foam" to --ppi foam--.

In Column 16, Line 42, change "mN/cm" to --mN/cm$^2$--.

In the Claims

In Column 32, Line 10 (Approx.), Claim 4, change "90%±5%." to --90±5%.--.

Signed and Sealed this
Ninth Day of July, 2019

Andrei Iancu
*Director of the United States Patent and Trademark Office*